US005858683A

United States Patent [19]
Keesee et al.

[11] Patent Number: 5,858,683
[45] Date of Patent: Jan. 12, 1999

[54] METHODS AND COMPOSITIONS FOR THE DETECTION OF CERVICAL CANCER

[75] Inventors: Susan K. Keesee, Harvard; Robert Obar, Walpole; Ying-Jye Wu, Framingham, all of Mass.

[73] Assignee: Matritech, Inc., Newton, Mass.

[21] Appl. No.: 705,660

[22] Filed: Aug. 30, 1996

[51] Int. Cl.$^6$ ..................................... G01N 33/53
[52] U.S. Cl. .................. 435/7.1; 435/7.2; 530/387.7; 530/388.8; 424/138.1
[58] Field of Search ............................. 424/132.1, 138.1; 435/7.1, 7.2; 530/388.8, 387.7

[56] References Cited

U.S. PATENT DOCUMENTS

| | | | |
|---|---|---|---|
| 4,474,893 | 10/1984 | Reading | 436/547 |
| 4,722,899 | 2/1988 | Hamaoka et al. | 435/172.2 |
| 4,775,620 | 10/1988 | Cardiff et al. | 435/7 |
| 4,882,268 | 11/1989 | Penman et al. | 435/5 |
| 4,885,236 | 12/1989 | Penman et al. | 435/6 |
| 5,091,513 | 2/1992 | Huston et al. | 530/387 |
| 5,098,890 | 3/1992 | Gerwirtz et al. | 514/44 |
| 5,273,877 | 12/1993 | Fey et al. | 435/6 |
| 5,350,835 | 9/1994 | Gaynor et al. | 530/358 |
| 5,547,928 | 8/1996 | Wu et al. | 514/2 |
| 5,688,511 | 11/1997 | Gaynor et al. | 424/207.1 |

FOREIGN PATENT DOCUMENTS

| | | |
|---|---|---|
| 62-084100 | 4/1987 | Japan . |
| WO 90/12885 | 11/1990 | WIPO . |
| WO 92/20702 | 11/1992 | WIPO . |
| WO 93/09437 | 5/1993 | WIPO . |
| WO 94/00573 | 1/1994 | WIPO . |
| WO 94/12881 | 6/1994 | WIPO . |
| WO 95/16919 | 6/1995 | WIPO . |
| WO 95/21252 | 8/1995 | WIPO . |

OTHER PUBLICATIONS

Seaver et al Genetic Engineering News vol. 14 No. 14 pp. 10 and 21, Aug. 1994.
Sevier et al Clinical Chemistry vol. 27 No. 11 1797–1806, 1981.
Smedts et al., "Basal–cell keratins in cervical reserve cells and a comparison to their expression in cervical intraepithelial neoplasia," *Am. J. Pathology*, 140(3):601–612, 1992.
Petrov et al., "The expression of cytokeratin No. 17 in squamous cell cancer of the cervix uteri: an immunohistochemical study of 19 cases," *Voprosy Onkologii*, 38(7):797–805 (1992), Abstract only.
Berezney et al., "Identification of a nuclear matrix protein", *Biochem. Biophys. Res. Commun.* 60:1410–1417 (1974).
Bidwell et al., "Nuclear Matrix Proteins Distinguish Normal Diploid Osteoblasts from Osteosarcoma Cells", *Cancer Research*, 54:28–32 (1994).
Bidwell et al., "Osteocalcin Gene Promoter Binding Factors are Tissue–Specific Nuclear Matrix Components," *Proc. Natl. Acad. Sci. USA* 90:3162–3166, 1993.
Brancolini et al., "Change in the Expression of a Nuclear Matrix–Associated Protein is Correlated with Cellular Transformation," *Proc. Natl. Acad. Sci. USA* 88:6936–6940 (1991).

Ciejak et al., "Actively Transcribed Genes are Associated with the Nuclear Matrix," *Nature* 306:607–609 (1983).
Donat et al., "Unique Nuclear Matrix Protein Alterations in Head and Neck Squamous Cell Carcinomas: Intermediate Biomarker Candidates," *Otolaryngol. Head Neck Surg.* 114:387–393 (1996).
Fey et al., "The Nuclear Matrix: Defining Structural and Functional Roles," *Eukaryotic Gene Expression*, 1:127–143 (1991).
Fey et al., "Nuclear Matrix Proteins Reflect Cell Type of Origin in Cultured Human Cells," *Proc. Natl. Acad. Sci. USA* 85:121–125 (1988).
Fisher et al., "cDNA Sequencing of Nuclear Lamins A and C Reveals Primary and Secondary Structural Homology to Intermediate Filament Proteins," *Proc. Natl. Acad. Sci. USA* 83:6450–6454 (1986).
Getzenberg et al., "Bladder Cancer–Associated Nuclear Matrix Proteins," *Cancer Res.* 56:690–694 (1996).
Getzenberg et al., "Identification of Nuclear Matrix Proteins in the Cancer and Normal Rat Prostate," *Cancer Res.* 51:6514–6520 (1991).
Getzenberg et al., "The Tissue Matrix: Cell Dynamics and Hormone Action," *Endocr. Rev.* :399–417 (1990).
Getzenberg et al., "Tissue Specificity of the Hormonal Response in Sex Accessory Tissues in Associated with Nuclear Matrix Protein Patterns," *Molecular Endocrinology* 1336–1342 (1990).
Greenfield et al., "Human Papillomavirus 16 E7 Protein Is Associated with the Nuclear Matrix," *Proc. Natl. Acad. Sci. USA* 88:11217–11221 (1991).
Honore et al., "Cloning of a cDNA Encoding a Novel Human Nuclear Phosphoprotein Belonging to the WD–40 Family," *Gene* 151:291–296 (1994).
Keesee et al., "Nuclear Matrix Proteins in Human Colon Cancer," *Proc. Natl. Acad. Sci. USA* 91:1913–1916 (1994).
Keesee et al., "Utilization of Nuclear Matrix Proteins for Cancer Diagnosis," *Critical Reviews in Eukaryotic Gene Expression* 6(2&3):189–214 (Jun 1996).

(List continued on next page.)

*Primary Examiner*—Sheela Huff
*Assistant Examiner*—Julie E. Reeves
*Attorney, Agent, or Firm*—Testa, Hurwitz & Thibeault, LLP

[57] ABSTRACT

The invention provides a wide range of methods and compositions for detecting and treating cervical cancer in an individual. Specifically, the invention provides target cervical cancer-associated proteins, which permit a rapid detection, preferably before metastases occur, of cervical cancer. The target cervical cancer-associated protein, may be detected, for example, by reacting the sample with a labeled binding moiety, for example, a labeled antibody capable of binding specifically to the protein. The invention also provides kits useful in the detection of cervical cancer in an individual. In addition, the invention provides methods utilizing the cervical cancer-associated proteins either as targets for treating cervical cancer or as indicators for monitoring of the efficacy of such a treatment.

23 Claims, 2 Drawing Sheets

OTHER PUBLICATIONS

Khanuja et al., "Nuclear Matrix Proteins in Normal and Breast Cancer Cells", *Cancer Research* 53:3394–3398 (1993).

Ou et al., "Cloning and Characterization of a Novel Cellular Protein, TDP–43, That Binds to Human Immunodeficiency Virus Type 1 TAR DNA Sequence Motifs," *J. of Virology* 69:3584–3596 (1995).

Pillai, R., "Oncogene Expression and Prognosis in Cervical Cancer," *Cancer Letters* 59:171–175 (1991).

Partin et al., "Nuclear Matrix Protein Patterns in Human Benign Prostatic Hyperplasia and Prostate Cancer," *Cancer Research* 53:744–746 (1993).

Stein et al., "Oligodeoxynucleotides as Inhibitors of Gene Expression: A Review," *Cancer Research* 48:2659–2668 (1988).

Stuurman et al, "The Nuclear Matrix from Cells of Different Origin," *Journal of Biological Chemistry* 265:5460–5465 (1990).

Troyanovsky et al., "Characterization of the Human Gene Encoding Cytokeratin 17 and its Expression Pattern," *European Journal of Cell Biology* 59:127–137 (1992).

Wu et al., "Nup358, a Cytoplasmically Exposed Nucleoporin with Peptide Repeats, Ran–GTP Binding Sites, Zinc Fingers, a Cyclophilin A Homologous Domain, and a Leucine–rich Region," *The Journal of Biological Chemistry* 270:14209–14213 (1995).

News Release; "Matritech Scientists Discover Specific Nuclear Matrix Proteins (NMPs) Associated with Cervical Cancer"; Aug. (1996).

Chiang et al., "Identification of a Tumor–Associated Antigen in Cervical Carcinoma by Two–Dimensional (Crossed) Immunoelectrophoresis," J. Natl. Cancer Inst., 58(1):43–48 (1977).

Adams et al., "Rapid cDNA Sequencing (Expressed Sequence Tags) From A Directionally Cloned Human Infant Brain cDNA Library," Nature Genetics, 4:373–380 (1993).

Nucifora et al., "Involvement of the AML1 Gene in the t(3;21) in Therapy–Related Leukemia and in Chronic Myeloid Leukemia in Blast Crisis," *Blood*, 81(10):2728–2734 (1993).

Lebel et al., "Lamin A is not Synthesized as a Larger Precursor Polypeptide," Biochemical and Biophysical Research Communications, 49(2):417–423(1987).

METHODS AND COMPOSITIONS FOR THE DETECTION OF CERVICAL CANCER

FIELD OF THE INVENTION

The present invention relates generally to methods and compositions for the detection of cervical cancer. More specifically, the present invention relates to cervical cancer-associated proteins which act as cellular markers useful (i) in detecting cervical cancer, and (ii) as molecular targets for cervical cancer therapy.

BACKGROUND OF THE INVENTION

Cancer of the uterine cervix is one of the most common malignancies in women and remains a significant public health problem throughout the world. In the United States alone, invasive cervical cancer accounts for approximately 19% of all gynecological cancers (Miller et al. (1993) in "*Surveillance Epidemiology, and End Results Program cancer Statistics Review*: 1973–1990", NIH Pub. No. 93–2789, Bethesda, Md.: National Cancer Institute). In 1996, it is estimated that there will be 14,700 newly diagnosed cases and 4900 deaths attributed to this disease (American Cancer Society, Cancer Facts & Figures 1996, Atlanta, Ga.: American Cancer Society, 1996). In many developing countries, where mass screening programs are not widely available, the clinical problem is more serious. Worldwide, the number of new cases is estimated to be 471,000 with a 4 year survival rate of 40% (Munoz et al. (1989) "*Epidemiology of Cervical Cancer*" in "*Human Papillomavirus*", New York, Oxford Press, pp 9–39; and National Institutes of Health, Consensus Development Conference Statement on Cervical Cancer, Apr.1–3, 1996).

The precursor to cervical cancer is dysplasia, also known in the art as cervical intraepithelial neoplasia (CIN) or squamous intraepithelial lesions (SIL) (Brinton et al. (1992) "*Epidemiology of Cervical Cancer. Overview*" in "*The Epidemiology of Cervical Cancer and Human Papillomavirus*", Lyon, France: International Agency for Research on Cancer; and Tabbara et al. (1992) "*The Bethesda classification for squamous intraepithelial lesions: histologic, cytologic and viral correlates*", Obstet. Gynecol 79: 338–346). While it is not understood how normal cells become transformed, the concept of a continuous spectrum of histopathological change from normal, stratified epithelium through CIN to invasive cancer has been widely accepted for many years (see, for example, Mitchell et al. (1994) "*The natural history of cervical intraepithelial neoplasia: an argument of intermediate endpoint biomarkers*", Cancer Epidmiol. Biomark. Prev. 3: 619–626). A large body of epidemiological and molecular biological evidence has been gathered that establishes human papillomavirus (HPV) infection as a causative factor in cervical cancer (Munoz et al. (1992) in "*The Epidemiology of Human Papillomavirus and Cervical Cancer*", IRAC publication no. 119, Lyon France: Int. Agency for Research on Cancer, pp 251–261). HPV is found in 85% or more of squamous cell invasive lesions, which represent the most common histologic type seen in cervical carcinoma (Cox et al. (1995) Baillierre's Clin. Obstet Gynaecol. 91–37). Additional cofactors include, for example, oncogenes activated by point mutations, and chromosomal translocations of deletions (Spandidos et al. (1989)J. Pathol. 157: 1–10).

Cytological examination of Papanicolaou-stained cervical smears (also referred to as Pap smears) currently is the method of choice for detecting cervical cancer. Despite the historical success of this test, concerns have arisen regarding its ability to predict reliably the behavior of same preinvasive lesions (Ostor et al. (1993) Int. J Gynecol. Pathol. 12: 186–192; and Genest et al. (1993) Human Pathol. 24: 730–736). The identification of a cervical cancer-associated tumor marker for reliably detecting early onset of cervical cancer and/or providing early prognostic information will greatly aid the management of cervical cancer.

All eukaryotic cells have a nucleus containing DNA, or chromatin, which is organized by an internal protein scaffolding known as the nuclear matrix (NM). The nuclear matrix was first described in 1974 by Berezney et al. (Berezney et al. (1974) Biochem. Biophys. Res. Commun., 60: 1410–1417). Penman et al. describe a method for selectively extracting insoluble interior nuclear matrix proteins and their associated nucleic acids from cells and determining the particular cell type by analyzing the proteins by two-dimensional gel electrophoresis (see for example, U.S. Pat. Nos. 4,882,268, issued Nov. 21, 1989, and 4,885, 236, issued Dec. 5, 1989, the disclosures of which are incorporated herein by reference).

The nuclear matrix is believed to be involved in a wide variety of nuclear functions fundamental to the control of gene expression. For a general review see, for example, Fey et al. (1991) Crit. Rev. Euk. Gene Express. 1: 127–143. Tissue-specific nuclear matrix proteins have been identified in the rat, mouse and human. Fey et al. (1986) Proc. Natl. Acad. Sci. USA 85: 121–125; Stuurman et al. (1990)J. Biol. Chem. 265: 5460–5465; and Getzenberg et al. (1990) Mol. Endocrinol. 4: 1336–1342. Changes in the presence or absence of specific nuclear matrix proteins have been associated with cellular transformation and differentiation (Bidwell et al. (1993) Proc. Natl. Acad. Sci. USA 90: 3162–3166; Brancolini et al. (1991) Proc. Natl. Acad. Sci. USA 88: 6936–6940; and Greenfield et al. (1991) Proc. Natl. Acad. Sci. USA 88: 11217–11221).

Several recent studies using similar methodology have identified tumor-specific nuclear matrix proteins in cancers of the prostate (Partin et al. (1993) Cancer Res. 53: 744–746), breast (Khanuja et al. (1993) Cancer Res. 53: 3394–3398), colon cancer (Keesee et al. (1994) Proc. Natl. Acad. Sci. USA 91: 1913–1916), bone (Bidwell et al. (1994) Cancer Res. 54: 28–32), bladder (Getzenberg et al. (1996) Cancer Res. 56: 690–694) and the larynx (Donat et al. (1996) Otolaryngol. Head Neck Surg. 114: 387–393). Molecular characterization of the specific nuclear matrix proteins, however, remains poorly defined, due to the low abundance of these proteins in the cell and their generally insoluble character.

There is, however, a need in the art for specific, reliable markers that are expressed differentially in normal and cancerous cervical tissue and that may be useful in the detecting cervical cancer or in the prediction of its onset. Accordingly, it is an object of this invention to provide cervical cancer-associated molecules which are useful as markers for the early and/or rapid detection of cervical cancers in an individual. It is another object of this invention to provide methods for detecting cervical cancers in an individual. It is another object of the invention to provide methods and compositions for treating cervical cancers in an individual and for monitoring the efficacy of such a treatment in the individual.

SUMMARY OF THE INVENTION

The invention provides a variety of methods and compositions for detecting and/or pregnosing cervical cancer in a tissue or body fluid sample of an individual. The invention is based, in part, upon the discovery of cervical cancer-associated proteins which are present at detectable levels in cervical cancer cells, but which are not detectable in normal cervical cells, as determined by two-dimensional gel electrophoresis.

In one aspect, the invention provides a method for detecting cervical cancer in a human. The method comprises the step of detecting the presence of a cervical cancer-associated protein in a tissue or body fluid sample of the human thereby to indicate the presence of a cervical cancer or a precursor of a cervical cancer. The cervical cancer-associated protein is characterized as having a molecular weight of from about 44,900 Daltons to about 69,400 Daltons, as determined by standard polyacrylamide gel electrophoresis techniques and an isoelectric point of from about 5.1 to about 6.6 as determined by standard isoelectric focusing techniques. In addition, the cervical cancer-associated protein is further characterized as being a non-chromatin protein which is detectable at a higher level in a human cervical cancer cell than in a normal human cervical cell, as determined by two-dimensional gel electrophoresis. It is contemplated, however, that the accuracy and/or reliability of the method may be further enhanced by detecting the presence of a plurality of cervical cancer-associated proteins in the preselected tissue or body fluid sample.

As used herein, the term "cervical cancer" is understood to mean any cancer or cancerous lesion associated with cervical tissue or cervical cells and, in addition, includes precursors to cervical cancer, for example, dysplasia (also known in the art as a cervical intraepithelial neoplasia or a squamous intraepithelial lesion).

As used herein, the term "cervical cancer-associated" molecules refers to molecules originating from and isolatable from a cervical cancer cell or cells, and substantially neither originating from nor isolatable from a normal cervical cell or cells. As used herein, the term "cervical cancer-associated protein" is understood to mean any protein which is detectable at a higher level in cervical cancer cells than in normal cervical cells, as determined by two-dimensional (2-D) gel electrophoresis. It is not necessary that the target molecule or target protein be unique to a cervical cancer cell; rather it is preferred that the target molecule or protein has a signal to noise ration high enough to discriminate between samples originating from a cervical cancer tissue or body fluid and samples originating from normal cervical tissue or body fluid.

In a preferred embodiment, methods of the invention comprise the step of detecting one or more cervical cancer (CvC) associated proteins, referred to herein as CvC-1 through CvC-5, which can be purified or co-purified using nuclear matrix protein purification methodologies, well known and thoroughly documented in the art. See, for example, Fey et al. (1986) *Proc. Natl. Acad Sci, USA* 85: 121–125, the disclosure of which is incorporated herein by reference. As used herein, the term "nuclear matrix protein" is understood to mean any non-cytoskeletal, non-lamin, non-chromatin protein that (i) is isolated from mammalian cell nuclei, (ii) is resistant to solubilization from the nuclei in 0.25M ammonium sulfate, (iii) remains in solution following dialysis into physiological buffer from 8M urea and (iv) is detectable on a silver stained two-dimensional electrophoresis gel. Accordingly, one or more of the resultant cervical cancer-associated proteins may be further defined as being a nuclear matrix protein.

In a preferred embodiment, methods of the invention may comprise the step of detecting the protein CvC-1, a protein having a molecular weight of about 69,400 Daltons, as determined by polyacrylamide gel electrophoresis, and a pI of about 5.8, as determined by isoelectric focusing techniques. Alternatively, the methods of the invention may comprise the step of detecting the protein CvC-2, a protein having a molecular weight of about 53,800 Daltons, as determined by polyacrylamide gel electrophoresis, and a pI of about 5.5, as determined by isoelectric focusing techniques. Alternatively, the methods of the invention may comprise the step of detecting the protein CvC-3, a protein having a molecular weight of about 47,900 Daltons, as determined by polyacrylamide gel electrophoresis, and a pI of about 5.6, as determined by isoelectric focusing techniques. Alternatively, the methods of the invention may comprise the step of detecting the protein CvC-4, a protein having a molecular weight of about 46,000 Daltons, as determined by polyacrylamide gel electrophoresis, and a pI of about 5.1, as determined by isoelectric focusing techniques. Alternatively, the methods of the invention may comprise the step of detecting the protein CvC-5, a protein having a molecular weight of about 44,900 Daltons, as determined by polyacrylamide gel electrophoresis, and a pI of about 6.6, as determined by isoelectric focusing techniques.

In another preferred embodiment, the methods of the invention may comprise the step of detecting a cervical cancer-associated protein which comprises a continuous amino acid sequence selected from the group consisting of: SEQ ID NO.: 1; SEQ ID NO.: 2; SEQ ID NO.: 3; SEQ ID NO.: 4; SEQ ID NO.: 5; SEQ ID NO.: 6; SEQ ID NO.: 7; SEQ ID NO.: 8; and SEQ ID NO.: 9. Alternatively, the method of the invention may comprise the step of detecting a cervical cancer-associated protein having the amino acid sequence set forth in SEQ ID NO.: 10, commonly referred to in the art as IEF SSP 9502. See, for example, Honore et al. (1994) *Gene* 151: 291–296, the disclosure of which is incorporated herein by reference.

In another preferred embodiment, the methods of the invention may comprise the step of detecting a cervical cancer-associated protein which comprises a continuous amino acid sequence selected from the group consisting of: SEQ ID NO.: 11; SEQ ID NO.: 12; SEQ ID NO.: 13; SEQ ID NO.: 14; SEQ ID NO.: 15; SEQ ID NO.: 16; and SEQ ID NO.: 17. Alternatively, the method of the invention may comprise the step of detecting a cervical cancer-associated protein having the amino acid sequence set forth in SEQ ID NO.: 18, and commonly referred to in the art as Cytokeratin 17. See, for example, Troyanovsky et al. (1992) *J. Biol. Biol.* 59: 127–137, the disclosure of which is incorporated herein by reference.

In another preferred embodiment, the methods of the invention may comprise the step of detecting a cervical cancer-associated protein which comprises a continuous amino acid sequence selected from the group consisting of: SEQ ID NO.: 19; SEQ ID NO.: 20; SEQ ID NO.: 21; SEQ ID NO.: 22; SEQ ID NO.: 23; SEQ ID NO.: 24; and SEQ ID NO.: 25. Alternatively, the method of the invention may comprise the step of detecting a cervical cancer-associated protein having the amino acid sequence set forth in SEQ ID NO.: 26, commonly referred to in the art as TDP-43. See, for example, Ou et al. (1995) *J. Virol.* 69: 3584–3596, the disclosure of which is incorporated herein by reference.

In another preferred embodiment, the methods of the invention may comprise the step of detecting a cervical cancer-associated protein which comprises a continuous amino acid sequence selected from the group consisting of: SEQ ID NO.: 27; SEQ ID NO.: 28; SEQ ID NO.: 29; SEQ ID NO.: 30; SEQ ID NO.: 31; SEQ ID NO.: 32; and SEQ ID NO.: 33. Alternatively, the method of the invention may comprise the step of detecting a cervical cancer-associated protein having the amino acid sequence set forth in SEQ ID NO.: 34, commonly referred to in the art as Nup358. See, for example, Wu et al. (1995) *J. Biol. Chem.* 270: 14209–14213, the disclosure of which is incorporated herein by reference.

In another preferred embodiment, the methods of the invention may comprise the step of detecting a cervical cancer-associated protein which comprises selected from s amino acid sequence selected from the group consisting of: SEQ ID NO.: 35; SEQ ID NO.: 36; SEQ ID NO.: 37; SEQ ID NO.: 38; SEQ ID NO.: 39; SEQ ID NO.: 40; SEQ ID NO.: 41; SEQ ID NO.: 42; SEQ ID NO.: 43; SEQ ID NO.: 44; and SEQ ID NO.: 45. Alternatively, the method of the invention may comprise the step of detecting a cervical cancer-associated protein having the amino acid sequence set forth in SEQ ID NO.: 46, commonly referred to in the art as lamin A. See, for example, Fisher et al. (1986) *Proc. Natl. Acad. Sci. USA.* 83: 6450–6454, the disclosure of which is incorporated herein by reference.

The methods of the invention may be performed on any relevant tissue or body fluid sample. For example, methods of the invention may be performed on cervical tissue, more preferably cervical biopsy tissue, and most preferably on Pap smears. Alternatively, the methods of the invention may be performed on a human body fluid sample selected from the group consisting of: blood; serum; plasma; fecal matter; urine; vaginal secretion; spinal fluid; saliva; ascitic fluid; peritoneal fluid; sputum; and breast exudate. It is contemplated, however, that the methods of the invention also may be useful in assays for metastasized cervical cancer cells in other tissue or body fluid samples.

Marker proteins associated with a cervical cancer in a tissue or body fluid sample may be detected using any of a number of assay methods available in the art. In one embodiment, for example, the marker cervical cancer-associated protein may be reacted with a labeled binding moiety capable of specifically binding to the marker protein thereby to produce a labeled complex of the binding moiety and the marker protein. The labeled complex thereafter may be detected, using conventional methodologies well known in the art. Detection of the presence of the labeled complex may provide an indication of the presence of the cervical cancer cells or pre-cancerous cells in the individual being tested. As used herein, the term "binding moiety" is understood to mean any binding partner capable of specifically binding to a cervical cancer-associated protein with a binding affinity greater than about $10^5 M^{-1}$. As used herein the terms "specifically binding", "specifically bound" and "binds specifically" refer to a binding interaction with a binding affinity of greater than about $10^5 M^{-1}$. As used herein, the binding moiety is labeled with a detectable moiety, for example, a radioactive, fluoroscopic, spectroscopic, or enzymatic label, using techniques well known in the art.

It is appreciated that, binding moieties which interact and bind specifically with the target protein, may be designed using conventional methods well known in the art. In the invention, the binding moiety can be an antibody, for example, a monoclonal or a polyclonal antibody. Monoclonal antibodies are preferred. It is contemplated, however, that other useful binding moieties useful in the practice of the instant invention may include, for example, biosynthetic antibody binding sites, also referred to in the art as BABS or sFv's, and antibody fragments, for example, Fv, Fab, Fab' and (Fab')$_2$ fragments. Procedures for preparing, testing, and labeling BABS and antibody fragments are well known in the art, and so are not discussed in detail herein.

In another embodiment, one or more marker proteins in a sample may be detected by first isolating the proteins from the sample, and then separating the proteins by two-dimensional gel electrophoresis to produce a characteristic two-dimensional gel electrophoresis pattern. The gel electrophoresis pattern then may be compared with a standard, for example, a standard gel pattern obtained from a data base of gel electrophoresis patterns. Thus, in another embodiment, the invention provides electrophoresis gel patterns or electropherograms of cervical cancer-associated proteins which are useful in detecting a cervical cancer in an individual.

The cervical cancer-associated proteins of the invention can be purified or co-purified from cervical cancer cells using nuclear matrix protein isolation procedures, such as those disclosed in U.S. Pat. No. 4,885,236 and U.S. Pat. No. 4,882,268, the disclosures of which are incorporated herein. Alternatively, the marker proteins, once identified and characterized may be isolated from the sample by any of a range of protein purification protocols well known to those skilled in the art, such as affinity chromatography, to yield isolated proteins. As used herein, the term "isolated" is understood to mean substantially free of undesired, contaminating proteinaceous material.

Furthermore, the skilled artisan may produce nucleic acid sequences encoding the entire isolated marker protein, or fragments thereof, using methods currently available in the art (see, for example, Maniatis et al., eds. (1989) "*Molecular Cloning: A Laboratory Manual,*" Cold Spring Harbor Press). For example, an isolated cervical cancer-associated protein may be sequenced using conventional peptide sequencing protocols, and then oligonucleotide hybridization probes designed for screening a cDNA library. The cDNA library then may be screened with the resultant oligonucleotide to isolate full or partial length CDNA sequences which encode the isolated protein.

Furthermore, the skilled artisan, using the methodologies described in U.S. Pat. Nos. 4,885,236 and 4,882,268 may isolate from a cell sample a nucleic acid molecule having a sequence capable of recognizing and being specifically bound by a cervical cancer-associated protein. In such a procedure, the soluble proteins are separated from the nucleus and cytoskeleton by extracting mammalian cells with a non-ionic detergent solution at physiological pH and ionic strength. The insoluble protein and nucleic acids then are digested with DNAase and then eluted with a buffered ammonium sulfate solution to yield a nucleic acid molecule capable of recognizing and being specifically bound by a cervical cancer-associated protein. Any remaining proteins then are separated from the target nucleic acid molecule.

Detection of the aforementioned nucleic acid molecules thus can serve as an indicator of the presence of cervical cancer and/or metastasized cervical cancer in an individual. Accordingly, in another aspect, the invention provides another method for detecting cervical cancer in a human. The method comprises the step of detecting the presence of a nucleic acid molecule in a tissue or body fluid sample thereby to indicate the presence of a cervical carcinoma in the individual. The nucleic acid molecule is selected from the group consisting of (i) a nucleic acid molecule comprising a sequence capable of recognizing and being specifically bound by a cervical cancer-associated protein, and (ii) a nucleic acid molecule comprising a sequence encoding a cervical cancer-associated protein. As defined herein, the cervical cancer-associated protein is characterized as being selected from the group consisting of (i) a protein having a molecular weight of about 69,400 Daltons and an isoelectric point of about 5.8; (ii) a protein having a molecular weight of about 53,800 Daltons and an isoelectric point of about 5.5; (iii) a protein having a molecular weight of about 47,900 Daltons and an isoelectric point of about 5.6; (iv) a protein having a molecular weight of about 46,000 Daltons, and an isoelectric point of about 5.1; and (v) a protein having a molecular weight of about 44,900 Daltons and an isoelectric point of about 6.6, wherein in each example, the molecular weight is determined by standard polyacrylamide gel electrophoresis techniques and the isoelectric point is determined by standard isoelectric focusing techniques, and wherein the cervical cancer-associated protein is further characterized as being a non-chromatin protein which is detectable at a higher level in a human cervical cancer cell than in a normal human cervical cell, as determined by two-dimensional gel electrophoresis.

A target nucleic acid molecule in a sample may be detected, for example, by Northern blot analysis by reacting the sample with a labeled hybridization probe, for example, a $^{32}$P labeled oligonucleotide probe, capable of hybridizing specifically with at least a portion of the nucleic acid molecule encoding the marker protein. Detection of a nucleic acid molecule either encoding a cervical cancer-associated protein or capable of being specifically bound by a cervical cancer-associated protein, thus can serve as an indicator of the presence of a cervical cancer in the individual being tested.

In another aspect, the invention provides a kit for detecting the presence of cervical cancer or for evaluating the efficacy of a therapeutic treatment of a cervical cancer. Such kits may comprise, in combination, (i) a receptacle for receiving a human tissue or body fluid sample from the individual, (ii) a binding partner which binds specifically either to an epitope on a marker cervical cancer-associated protein or a nucleic acid sequence encoding at least a portion of the marker cervical cancer-associated protein, (iii) means for detecting the binding of the binding partner with either the cervical cancer-associated protein or the nucleic acid sequence encoding at least a portion of the cervical cancer-associated protein, and (iv) a reference sample.

In one embodiment of the kit, the binding moiety binds specifically to a cervical cancer-associated protein selected from the group of proteins further defined as having: a molecular weight of about 69,400 Daltons and an isoelectric point of about 5.8; a molecular weight of about 53,800 Daltons and an isoelectric point of about 5.5; a molecular weight of about 47,900 Daltons and an isoelectric point of about 5.6; a molecular weight of about 46,000 Daltons and an isoelectric point of about 5.1, or a molecular weight of about 44,900 Daltons and an isoelectric point of about 6.6, wherein the molecular weight is determined by conventional polyacrylamide gel electrophoresis methodologies, and the isoelectric point is determined by conventional isoelectric focusing methodologies.

In another embodiment of the kit, the reference sample may comprise a negative and/or positive control. The negative control being indicative of a normal cervical cell type and the positive control being indicative of cervical cancer.

In another aspect, the invention provides a method for treating cervical cancer. The method comprises administering to a patient with cervical cancer, a therapeutically-effective amount of a compound, preferably an antibody, and most preferably a monoclonal antibody, which binds specifically to a target cervical cancer-associated protein thereby to inactivate the protein. The target protein being characterized as having a molecular weight of from about 44,900 Daltons to about 69,400 Daltons, as determined by standard polyacrylamide gel electrophoresis techniques and an isoelectric point of from about 5.1 to about 6.6, as determined by standard isoelectric focusing techniques, and wherein the target protein is further characterized as being a non-chromatin protein which is detectable at a higher level in a human cervical cancer cell than in a normal human cervical cell, as determined by two-dimensional gel electrophoresis. Similarly, it is contemplated that the compound may comprise a small molecule, for example, as small organic molecule, which inhibits or reduces the biological activity of the target cervical cancer-associated protein.

In another aspect, the invention provides another method for treating cervical cancer. The method comprises the step of administering to a patient diagnosed as having cervical cancer, a therapeutically-effective amount of a compound which reduces in vivo the expression of a target cervical cancer-associated protein thereby to reduce in vivo the expression of the target protein. In a preferred embodiment, the compound is a nucleobase containing sequence, such as, an anti-sense nucleic acid sequence or anti-sense peptide nucleic acid (PNA) molecule, complementary to a nucleic acid sequence encoding at least a portion of the target protein. After administration, the anti-sense nucleic acid sequence or anti-sense PNA molecule binds to the nucleic acid sequences encoding, at least in part, the target protein thereby to reduce in vivo expression of the target cervical cancer-associated protein.

Thus, the invention provides a wide range of methods and compositions for detecting and treating cervical cancer in an individual. Specifically, the invention provides cervical cancer-associated proteins, which permit specific and early, preferably before metastases occur, detection of cervical cancer in an individual. In addition, the invention provides kits useful in the detection of cervical cancer in an individual. In addition, the invention provides methods utilizing the cervical cancer-associated proteins as targets and indicators, for treating cervical cancers and for monitoring of the efficacy of such a treatment. These and other numerous additional aspects and advantages of the invention will become apparent upon consideration of the following figures, detailed description, and claims which follow.

Figure 1A:
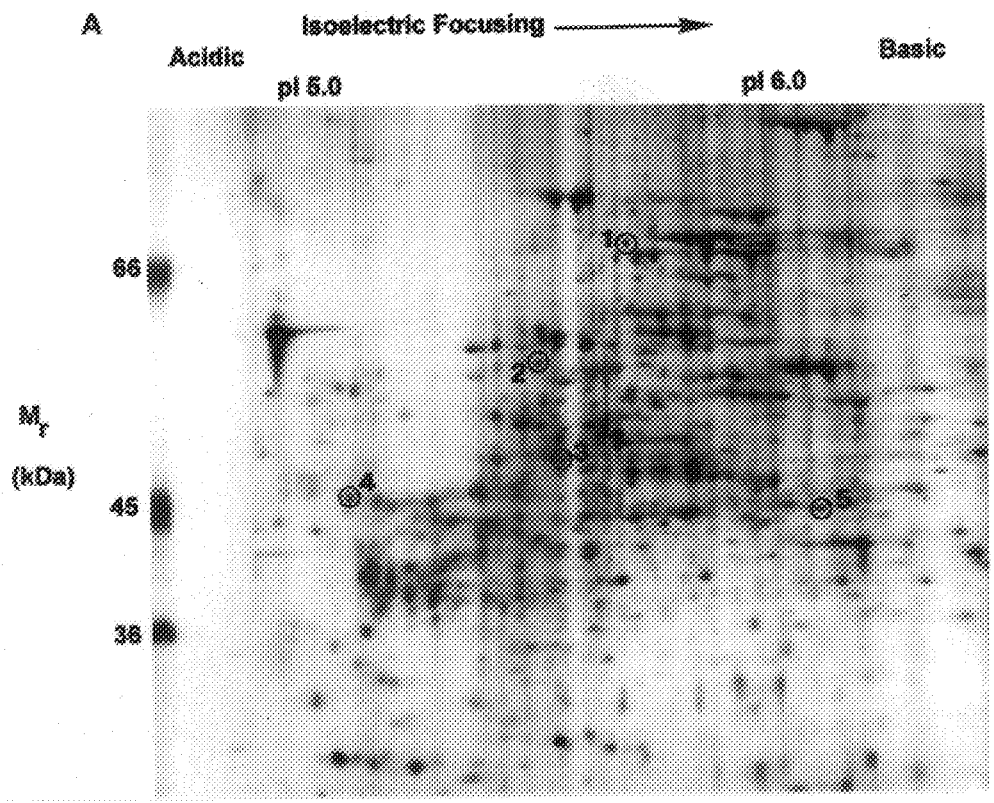
FIG. 1a is a high resolution two-dimensional gel electrophoresis pattern of nuclear matrix proteins isolated from a cervical cancer tissue sample. Tumor-associated proteins encircled and marked with reference numbers 1–5 correspond to proteins CvC-1 to CvC-5, listed in Table 2.

For each of the above figures, molecular weight standards are indicated on the ordinate axes ($M_r \times 10^3$) and isoelectric points are shown on the abscissae.

DETAILED DESCRIPTION OF THE INVENTION

The present invention provides methods and compositions for the detection and treatment of cervical cancer. The invention is based, in part, upon the discovery of cervical cancer-associated proteins which generally are present at detectably higher levels in cancerous cervical cells than in normal cervical cells, as determined by two-dimensional gel electrophoresis.

The cervical cancer-associated proteins may act as marker proteins useful in the detection of cervical cancer or as target proteins for therapy of cervical cancer. For example, it is contemplated that, the marker proteins and binding moieties, for example, antibodies that bind to the marker proteins or nucleic acid probes which hybridize to nucleic acid sequences encoding the marker proteins, may be used to detect the presence of cervical cancer in an individual. Furthermore, it is contemplated that, the skilled artisan may produce novel therapeutics for treating cervical cancer which include, for example: antibodies which can be administered to an individual that bind to and reduce or eliminate the biological activity of the target protein in vivo; nucleic acid or peptide nucleic acid sequences which hybridize with genes or gene transcripts encoding the target proteins thereby to reduce expression of the target proteins in vivo, or small molecules, for example, organic molecules which interact with the target proteins or other cellular moieties, for example, receptors for the target proteins, thereby to reduce or eliminate biological activity of the target proteins.

Set forth below are methods for isolating cervical cancer-associated proteins, methods for detecting cervical cancer using cervical cancer-associated proteins as markers, and methods for treating individuals afflicted with cervical cancer using cervical cancer-associated proteins as targets for cancer therapy.

1. Identification and Purification of Cervical Cancer-associated Proteins

Marker proteins of the invention, as disclosed herein are identified by (i) isolating proteins from normal cervical tissue and from cervical cancer tissue using a nuclear matrix purification protocol, such as those described generally in U.S. Pat. Nos. 4,882,268 and 4,885,236, or Fey et al. (1986) supra (ii) fractionating the resulting nuclear matrix protein preparations by 2-D gel electrophoresis, (iii) visualizing the resulting protein patterns, for example, by silver staining, and (iv) identifying polypeptide spots on the resulting 2-D gel electropherograms which generally are detectable in samples isolated from cervical cancer cells but not detectable in samples isolated from normal cervical cells.

Marker proteins associated with cervical cancer tissue were isolated as described herein using a modification of the method of Fey et al. (Fey et al. (1986) supra). Briefly, cervical cancer tissue is minced into small (1 mm³) pieces and homogenized with a Teflon pestle on ice and treated with a buffered solution containing 0.5% Triton-X-100, vanadyl riboside complex plus a protease inhibitor cocktail (phenylmethyl sulfonyl fluoride, aprotinin, and leupeptin) to remove lipids and soluble proteins. Tumor cells from cell lines can be harvested by trypsinization and treated in the same way as for homogenized tumor tissue. Stromal aggregates are removed by filtering the homogenate through a 250 micron nylon screen followed by a centrifugation step.

Soluble cytoskeletal proteins are removed by incubating the pellet in an extraction buffer containing 250 mM $(NH_4)_2SO_4$, 0.5% Triton-X-100, vanadyl riboside complex plus a protease inhibitor cocktail for 10 minutes on ice followed by centrifugation. Chromatin is removed by incubating the pellet in DNAase I in a buffered solution containing a protease inhibitor cocktail for 45 minutes at 25° C.

The remaining pellet fraction, containing the target proteins and intermediate filaments, is solubilized in a disassembly buffer containing 8M urea, protease inhibitor cocktail plus 1% 2-mercaptoethanol. Insoluble contaminants, primarily carbohydrates and extracellular matrix, are removed by ultracentrifugation. Intermediate filaments are allowed to reassemble upon removal of urea by dialysis in assembly buffer containing protease inhibitor cocktail and removed by ultracentrifugation, leaving the target proteins in the supernatant fraction. Protein concentration can be determined by the Coomassie Plus Protein Assay Kit (Pierce Chemicals, Rockford, Ill.) using a bovine gamma globulin standard. Proteins are immediately precipitated in 80% ethanol and stored at −80° C. until use.

It is contemplated that, after identification, the resulting cervical cancer-associated proteins may be isolated by preparing a nuclear matrix protein preparation, such as the one described above, electrophoresing the resulting proteins on a 2-D gel, and after some means of visualization, isolating the protein of interest from the resulting 2-D gel. Alternatively, it is contemplated that the marker protein, once identified, can be isolated, using standard protein purification methodologies well known to those of ordinary skill in the art, such as affinity chromatography, to yield substantially pure marker proteins. As used herein, the term "substantially pure" is understood to mean at least 80% pure as determined by sodium dodecyl sulfate-polyacrylamide gel electrophoresis (SDS-PAGE).

2. Detection of Cervical Cancer

Once cervical cancer-associated proteins have been identified, they may be used as markers to determine whether an individual has cervical cancer and/or cervical dysplasia, and if so, suitable detection methods can be used to monitor the status of the disease.

Using the marker proteins, the skilled artisan can produce a variety of detection methods for detecting cervical cancer in a human. The methods, typically comprise the steps of detecting, by some means, the presence of one or more cervical cancer-associated proteins in a tissue or body fluid sample of the human. The accuracy and/or reliability of the method for detecting cervical cancer in a human may be further enhanced by detecting the presence of a plurality of cervical cancer-associated proteins in a preselected tissue or body fluid sample. The detection step may comprise one or more of the protocols described hereinbelow.

2.A. Protein Detection Methods.

The marker protein in a sample may be reacted with a binding moiety capable of specifically binding the marker protein. The binding moiety may comprise, for example, a member of a ligand-receptor pair, i.e., a pair of molecules capable of having a specific binding interaction. The binding moiety may comprise, for example, a member of a specific binding pair, such as antibody-antigen, enzyme-substrate, nucleic acid-nucleic acid, protein-nucleic acid, protein—protein, or other specific binding pair known in the art. Binding proteins may be designed which have enhanced affinity for a target protein. Optionally, the binding moiety may be linked with a detectable label, such as an enzymatic, fluorescent, radioactive, phosphorescent or colored particle label. The labeled complex may be detected, e.g., visually or with the aid of a spectrophotometer or other detector.

The marker proteins also may be detected using gel electrophoresis techniques available in the art. In two-dimensional gel electrophoresis, the proteins are separated first in a pH gradient gel according to their isoelectric point. The resulting gel then is placed on a second polyacrylamide gel, and the proteins separated according to molecular weight (see, for example, O'Farrell (1975) *J. Biol. Chem.* 250: 4007–4021).

One or more marker proteins may be detected by first isolating proteins from a sample obtained from an individual suspected of having cervical cancer, and then separating the proteins by two-dimensional gel electrophoresis to produce a characteristic two-dimensional gel electrophoresis pattern. The pattern then may be compared with a standard gel pattern produced by separating, under the same or similar conditions, proteins isolated from normal or cancer cells. The standard may be stored or obtained in an electronic database of electrophoresis patterns. The presence of a cervical cancer-associated protein in the two-dimensional gel provides an indication of the presence of a cervical cancer in the sample being tested. The detection of two or more proteins in the two-dimensional gel electrophoresis pattern further enhances the accuracy of the assay. The presence of a plurality, e.g., two to five, cervical cancer-associated proteins on the two-dimensional gel provides a strong indication of the presence of a cervical cancer in the sample. The assay thus permits the early detection and treatment of cervical cancer.

2B. Immunoassay.

A marker cervical cancer-associated protein may also be detected using any of a wide range of immunoassay techniques available in the art. For example, the skilled artisan may employ the sandwich immunoassay format to detect cervical cancer in a body fluid sample. Alternatively, the skilled artisan may use conventional immuno-histochemical procedures for detecting the presence of the cervical cancer-associated protein in a tissue sample, for example, in a Pap smear, using one or more labeled binding proteins (See Example 5, hereinbelow).

In a sandwich immunoassay, two antibodies capable of binding the marker protein generally are used, e.g., one immobilized onto a solid support, and one free in solution and labeled with detectable chemical compound. Examples of chemical labels that may be used for the second antibody include radioisotopes, fluorescent compounds, and enzymes or other molecules which generate colored or electrochemically active products when exposed to a reactant or enzyme substrate. When a sample containing the marker protein is placed in this system, the marker protein binds to both the immobilized antibody and the labeled antibody, to form a "sandwich" immune complex on the support's surface. The complexed protein is detected by washing away non-bound sample components and excess labeled antibody, and measuring the amount of labeled antibody complexed to protein on the support's surface.

Both the sandwich immunoassay and the tissue immunohistochemical procedure are highly specific and very sensitive, provided that labels with good limits of detection are used. A detailed review of immunological assay design, theory and protocols can be found in numerous texts in the art, including *"Practical Immunology"*, Butt, W. R., ed., (1984) Marcel Dekker, New York and *"Antibodies, A Laboratory Approach"* Harlow et al. eds.(1988) Cold Spring Harbor Laboratory.

In general, immunoassay design considerations include preparation of antibodies (e.g., monoclonal or polyclonal antibodies) having sufficiently high binding specificity for the target protein to form a complex that can be distinguished reliably from products of nonspecific interactions.

As used herein, the term "antibody" is understood to mean binding proteins, for example, antibodies or other proteins comprising an immunoglobulin variable region-like binding domain, having the appropriate binding affinities and specificities for the target protein. The higher the antibody binding specificity, the lower the target protein concentration that can be detected. A preferred binding specificity is such that the binding protein has a binding affinity for the target protein of greater than about $10^5 M^{-1}$, preferably greater than about $10^7 M^{-1}$.

Antibodies to an isolated target cervical cancer-associated protein which are useful in assays for detecting a cervical cancer in an individual may be generated using standard immunological procedures well known and described in the art. See, for example, *Practical Immunology*, Butt, N. R., ed., Marcel Dekker, N.Y., 1984. Briefly, an isolated target protein is used to raise antibodies in a xenogeneic host, such as a mouse, goat or other suitable mammal.

The marker protein is combined with a suitable adjuvant capable of enhancing antibody production in the host, and injected into the host, for example, by intraperitoneal administration. Any adjuvant suitable for stimulating the host's immune response may be used. A commonly used adjuvant is Freund's complete adjuvant (an emulsion comprising killed and dried microbial cells and available from, for example, Calbiochem Corp., San Diego, or Gibco, Grand Island, N.Y.). Where multiple antigen injections are desired, the subsequent injections comprise the antigen in combination with an incomplete adjuvant (e.g., cell-free emulsion).

Polyclonal antibodies may be isolated from the antibody-producing host by extracting serum containing antibodies to the protein of interest. Monoclonal antibodies may be produced by isolating host cells that produce the desired antibody, fusing these cells with myeloma cells using standard procedures known in the immunology art, and screening for hybrid cells (hybridomas) that react specifically with the target protein and have the desired binding affinity.

Antibody binding domains also may be produced biosynthetically and the amino acid sequence of the binding domain manipulated to enhance binding affinity with a preferred epitope on the target protein. Specific antibody methodologies are well understood and described in the literature. A more detailed description of their preparation can be found, for example, in *"Practical Immunology"* (1984) supra)

In addition, genetically engineered biosynthetic antibody binding sites, also known in the art as BABS or sFv's, may be used in the practice of the instant invention. Methods for making and using BABS comprising (i) non-covalently associated or disulfide bonded synthetic $V_H$ and $V_L$ dimers, (ii) covalently linked $V_H$-$V_L$ single chain binding sites, (iii) individual $V_H$ or $V_L$ domains, or (iv) single chain antibody binding sites are disclosed, for example, in U.S. Pat. Nos.: 5,091,513; 5,132,405; 4,704,692; and 4,946,778, the disclosures of which are incorporated herein by reference. Furthermore, BABS having requisite specificity for the cervical cancer-associated proteins can be derived by phage antibody cloning from combinatorial gene libraries (see, for example, Clackson et al. (1991) *Nature* 352: 624–628). Briefly, a library of phage each of which express on their coat surface, BABS having immunoglobulin variable regions encoded by variable region gene sequences derived from mice pre-immunized with isolated cervical cancer-associated proteins, or fragments thereof, are screened for binding activity against immobilized cervical cancer-associated protein. Phage which bind to the immobilized cervical cancer-associated proteins are harvested and the gene encoding the BABS sequenced. The resulting nucleic acid sequences encoding the BABS of interest then may be expressed in conventional expression systems to produce the BABS protein.

The isolated cervical cancer-associated protein also may be used for the development of diagnostic and other tissue evaluating kits and assays to monitor the level of the proteins in a tissue or fluid sample. For example, the kit may include antibodies or other specific binding proteins which bind specifically with the cervical cancer-associated proteins and which permit the presence and/or concentration of the cervical cancer-associated proteins to be detected and/or quantitated in a tissue or fluid sample.

Suitable kits for detecting cervical cancer-associated proteins are contemplated to include, e.g., a receptacle or other means for capturing a sample to be evaluated, and means for detecting the presence and/or quantity in the sample of one or more of the cervical cancer-associated proteins described herein. As used herein, "means for detecting" in one embodiment includes one or more antibodies specific for these proteins and means for detecting the binding of the antibodies to these proteins by, e.g., a standard sandwich immunoassay as described herein. Where the presence of a protein within a cell is to be detected, e.g., as from a tissue sample, the kit also may comprise means for disrupting the cell structure so as to expose intracellular proteins.

2.C. Nucleic Acid-based Assays.

The presence of a cervical cancer in an individual also may be determined by detecting, in a tissue or body fluid sample, a nucleic acid molecule encoding a cervical cancer-associated protein. Using methods well known to those of ordinary skill in the art, the cervical cancer-associated proteins of the invention may be sequenced, and then, based on the determined sequence, oligonucleotide probes designed for screening a cDNA library (see, for example, Maniatis et al. (1989) supra).

A target nucleic acid molecule encoding a marker cervical cancer-associated protein may be detected using a labeled binding moiety, capable of specifically binding the target nucleic acid. The binding moiety may comprise, for example, a protein, a nucleic acid or a peptide nucleic acid. Additionally, a target nucleic acid, such as an mRNA encoding a cervical cancer-associated protein, may be detected by conducting, for example, a Northern blot analysis using labeled oligonucleotides, e.g., nucleic acid fragments complementary to and capable of hybridizing specifically with at least a portion of a target nucleic acid. While any length oligonucleotide may be utilized to hybridize an mRNA transcript, oligonucleotides typically within the range of 8–100 nucleotides, preferably within the range of 15–50 nucleotides, are envisioned to be most useful in standard hybridization assays.

The oligonucleotide selected for hybridizing to the target nucleic acid, whether synthesized chemically or by recombinant DNA methodologies, is isolated and purified using standard techniques and then preferably labeled (e.g., with $^{35}S$ or $^{32}P$) using standard labeling protocols. A sample containing the target nucleic acid then is run on an electrophoresis gel, the dispersed nucleic acids transferred to a nitrocellulose filter and the labeled oligonucleotide exposed to the filter under suitable hybridizing conditions, e.g. 50% formamide, 5×SSPE, 2×Denhardt's solution, 0.1% SDS at 42° C., as described in Maniatis et al. (1989) supra. Other useful procedures known in the art include solution hybridization, and dot and slot RNA hybridization. The amount of the target nucleic acid present in a sample optionally then is quantitated by measuring the radioactivity of hybridized fragments, using standard procedures known in the art.

In addition, oligonucleotides also may be used to identify other sequences encoding members of the target protein families. The methodology also may be used to identify genetic sequences associated with the nucleic acid sequences encoding the proteins described herein, e.g., to identify non-coding sequences lying upstream or downstream of the protein coding sequence, and which may play a functional role in expression of these genes. Additionally, binding assays may be conducted to identify and detect proteins capable of a specific binding interaction with a nucleic acid encoding a cervical cancer-associated protein, which may be involved e.g., in gene regulation or gene expression of the protein. In a further embodiment, the assays described herein may be used to identify and detect nucleic acid molecules comprising a sequence capable of recognizing and being specifically bound by a cervical cancer-associated protein.

In addition, it is anticipated that using a combination of appropriate oligonucleotide primers, i.e., more than one primer, the skilled artisan may determine the level of expression of a target gene in vivo by standard polymerase chain reaction (PCR) procedures, for example, by quantitative PCR. Conventional PCR based assays are discussed, for example, in Innes et al (1990) "PCR Protocols; A guide to methods and Applications", Academic Press and Innes et al. (1995) "PCR Strategies" Academic Press, San Diego, Calif.

3. Identification of Proteins Which Interact In Vivo With Cervical Cancer-associated Proteins In addition, it is contemplated that the skilled artisan, using procedures like those described hereinbelow, may identify other molecules which interact in vivo with the cervical cancer-associated proteins described herein. Such molecules also may provide possible targets for chemotherapy.

By way of example, cDNA encoding proteins or peptides capable of interacting with cervical cancer-associated proteins can be determined using a two-hybrid assay, as reported in Durfee et al. (1993) Genes & Develop. 7: 555–559, the disclosure of which is incorporated herein by reference. The principle of the two hybrid system is that noncovalent interaction of two proteins triggers a process (transcription) in which these proteins normally play no direct role, because of their covalent linkage to domains that function in this process. For example, in the two-hybrid assay, detectable expression of a reporter gene occurs when two fusion proteins, one comprising a DNA-binding domain and one comprising a transcription initiation domain, interact.

The skilled artisan can use a host cell that contains one or more reporter genes, such as yeast strain Y153, reported in Durfee et al. (1993) supra. This strain carries two chromosomally located reporter genes whose expression is regulated by Gal4. A first reporter gene, is the E. coli lacZ gene under the control of the Gal4 promoter. A second reporter gene is the selectable HIS3 gene. Other useful reporter genes may include, for example, the luciferase gene, the LEU2 gene, and the GFP (Green Fluorescent Protein) gene.

Two sets of plasmids are used in the two hybrid system. One set of plasmids contain DNA encoding a Gal4 DNA-binding domain fused in frame to DNA encoding a cervical cancer-associated protein. The other set of plasmids contain DNA encoding a Gal4 activation domain fused to portions of a human cDNA library constructed from human lymphocytes. Expression from the first set of plasmids result in a fusion protein comprising a Gal4 DNA-binding domain and a cervical cancer-associated protein. Expression from the second set of plasmids produce a transcription activation protein fused to an expression product from the lymphocyte cDNA library. When the two plasmids are transformed into a gal-deficient host cell, such as the yeast Y153 cells described above, interaction of the Gal DNA binding domain and transcription activation domain occurs only if the cervical cancer-associated protein fused to the DNA binding domain binds to a protein expressed from the lymphocyte cDNA library fused to the transcription activating domain. As a result of the protein-protein interaction between the cervical cancer-associated protein and its in vivo binding partner detectable levels of reporter gene expression occur.

In addition to identifying molecules which interact in vivo with the cervical cancer-associated proteins, the skilled artisan may also screen for molecules, for example, small molecules which alter or inhibit specific interaction between a cervical cancer-associated protein and its in vivo binding partner.

For example, host cell can be transfected with DNA encoding a suitable DNA binding domain/cervical cancer-associated protein hybrid and a translation activation domain/putative cervical cancer-associated protein binding partner, as disclosed above. The host cell also contains a suitable reporter gene in operative association with a cis-acting transcription activation element that is recognized by the transcription factor DNA binding domain. The level of reporter gene expressed in the system is assayed. Then, the host cell is exposed to a candidate molecule and the level of reporter gene expression is detected. A reduction in reporter gene expression is indicative of the candidate's ability to interfere with complex formation or stability with respect to the cervical cancer-associated protein and its in vivo binding partner. As a control, the candidate molecule's ability to interfere with other, unrelated protein-protein complexes is also tested. Molecules capable of specifically interfering with a cervical cancer-associated protein/binding partner interaction, but not other protein-protein interactions, are identified as candidates for production and further analysis. Once a potential candidate has been identified, its efficacy in modulating cell cycling and cell replication can be assayed in a standard cell cycle model system.

Candidate molecules can be produced as described hereinbelow. For example, DNA encoding the candidate molecules can be inserted, using conventional techniques well described in the art (see, for example, Maniatis (1989) supra) into any of a variety of expression vectors and transfected into an appropriate host cell to produce recombinant proteins, including both full length and truncated forms. Useful host cells include *E. coli, Saccharomyces cerevisiae, Pichia pastoris*, the insect/baculovirus cell system, myeloma cells, and various other mammalian cells. The full length forms of such proteins are preferably expressed in mammalian cells, as disclosed herein. The nucleotide sequences also preferably include a sequence for targeting the translated sequence to the nucleus, using, for example, a sequence encoding the eight amino acid nucleus targeting sequence of the large T antigen, which is well characterized in the art. The vector can additionally include various sequences to promote correct expression of the recombinant protein, including transcription promoter and termination sequences, enhancer sequences, preferred ribosome binding site sequences, preferred mRNA leader sequences, preferred protein processing sequences, preferred signal sequences for protein secretion, and the like. The DNA sequence encoding the gene of interest can also be manipulated to remove potentially inhibiting sequences or to minimize unwanted secondary structure formation. As will be appreciated by the practitioner in the art, the recombinant protein can also be expressed as a fusion protein.

After translation, the protein can be purified from the cells themselves or recovered from the culture medium. The DNA can also include sequences which aid in expression and/or purification of the recombinant protein. The DNA can be expressed directly or can be expressed as part of a fusion protein having a readily cleavable fusion junction.

The DNA may also be expressed in a suitable mammalian host. Useful hosts include fibroblast 3T3 cells, (e.g., NIH 3T3, from CRL 1658) COS (simian kidney ATCC, CRL-1650) or CH0 (Chinese hamster ovary) cells (e.g., CHO-DXB11, from Chasin (1980) *Proc. Nat'l. Acad. Sci. USA* 77 :4216–4222), mink-lung epithelial cells (MV1Lu), human foreskin fibroblast cells, human glioblastoma cells, and teratocarcinoma cells. Other useful eukaryotic cell systems include yeast cells, the insect/baculovirus system or myeloma cells.

In order to express a candidate molecule, the DNA is subcloned into an insertion site of a suitable, commercially available vector along with suitable promoter/enhancer sequences and 3' termination sequences. Useful promoter/enhancer sequence combinations include the CMV promoter (human cytomegalovirus (MIE) promoter) present, for example, on pCDM8, as well as the mammary tumor virus promoter (MMTV) boosted by the Rous sarcoma virus LTR enhancer sequence (e.g., from Clontech, Inc., Palo Alto). A useful inducable promoter includes, for example, A $Zn^{2+}$ induceable promoter, such as the $Zn^{2+}$ metallothionein promoter (Wrana et al. (1992) Cell 71: 1003–1014) Other induceable promoters are well known in the art and can be used with similar success. Expression also can be further enhanced using trans-activating enhancer sequences. The plasmid also preferably contains an amplifiable marker, such as DHFR under suitable promoter control, e.g., SV40 early promoter (ATCC #37148). Transfection, cell culturing, gene amplification and protein expression conditions are standard conditions, well known in the art, such as are described, for example in Ausubel et al., ed.,(1989) *"Current Protocols in Molecular Biology"*, John Wiley & Sons, N.Y. Briefly, transfected cells are cultured in medium containing 5–10% dialyzed fetal calf serum (dFCS), and stably transfected high expression cell lines obtained by amplification and subcloning and evaluated by standard Western and Northern blot analysis. Southern blots also can be used to assess the state of integrated sequences and the extent of their copy number amplification.

The expressed candidate protein is then purified using standard procedures. A currently preferred methodology uses an affinity column, such as a ligand affinity column or an antibody affinity column. The column is then washed, and the candidate molecules selectively eluted in a gradient of increasing ionic strength, changes in pH, or addition of mild detergent. It is appreciated that in addition to the candidate molecules which bind to the cervical cancer-associated proteins, the cervical cancer associated proteins themselves may likewise be produced using such recombinant DNA technologies.

4. Cervical Cancer Therapy and Methods-for Monitoring Therapy

The skilled artisan, after identification of cervical cancer-associated proteins and proteins which interact with the cervical cancer-associated proteins, can develop a variety of therapies for treating cervical cancer. Because the marker proteins described herein are present at detectably higher levels in cervical cancer cells relative to normal cervical cells, the skilled artisan may employ, for example, the marker proteins and/or nucleic acids encoding the marker proteins as target molecules for a cancer chemotherapy.

4.A. Anti-sense-based Therapeutics.

A particularly useful cancer therapeutic envisioned is an oligonucleotide or peptide nucleic acid sequence complementary and capable of hybridizing under physiological conditions to part, or all, of the gene encoding the marker protein or to part, or all, of the transcript encoding the marker protein thereby to reduce or inhibit transcription and/or translation of the marker protein gene. Alternatively, the same technologies may be applied to reduce or inhibit transcription and/or translation of the proteins which interact with the cervical cancer-associated proteins.

Anti-sense oligonucleotides have been used extensively to inhibit gene expression in normal and abnormal cells. See, for example, Stein et al. (1988) *Cancer Res.* 48: 2659–2668, for a pertinent review of anti-sense theory and established protocols. In addition, the synthesis and use of peptide nucleic acids as anti-sense-based therapeutics are described in PCT publications PCT/EP92/01219 published Nov. 26, 1992, PCT/US92/10921 published Jun. 24, 1993, and PCT/US94/013523 published Jun. 1, 1995, the disclosures of which are incorporated herein by reference. Accordingly, the anti-sense-based therapeutics may be used as part of chemotherapy, either alone or in combination with other therapies.

Anti-sense oligonucleotide and peptide nucleic acid sequences are capable of hybridizing to a gene and/or mRNA transcript and, therefore, may be used to inhibit transcription and/or translation of the protein described herein. It is appreciated, however, that oligoribonucleotide sequences generally are more susceptible to enzymatic attack by ribonucleases than are deoxyribonucleotide sequences. Hence, oligodeoxyribonucleotides are preferred over oligoribonucleotides for in vivo therapeutic use. It is appreciated that the peptide nucleic acid sequences, unlike regular nucleic acid sequences, are not susceptible to nuclease degradation and, therefore, are likely to have greater longevity in vivo. Furthermore, it is appreciated that peptide nucleic acid sequences bind complementary single stranded DNA and RNA strands more strongly than corresponding DNA sequences (see, for example, PCT/EP92/20702 published Nov. 26, 1992). Accordingly, peptide nucleic acid sequences are preferred for in vivo therapeutic use.

Therapeutically useful anti-sense oligonucleotides or peptide nucleic acid sequences may be synthesized by any of the known chemical oligonucleotide and peptide nucleic acid synthesis methodologies well known and thoroughly described in the art. Alternatively, a complementary sequence to part or all of the natural mRNA sequence may be generated using standard recombinant DNA technologies.

Since the complete nucleotide sequence encoding the entire marker protein as well as additional 5' and 3' untranslated sequences are known for each of the marker proteins and/or can be determined readily using techniques well known in the art, anti-sense oligonucleotides or peptide nucleic acids which hybridize with any portion of the mRNA transcript or non-coding sequences may be prepared using conventional oligonucleotide and peptide nucleic acid synthesis methodologies.

Oligonucleotides complementary to, and which hybridizable with any portion of the mRNA transcripts encoding the marker proteins are, in principle, effective for inhibiting translation of the target proteins as described herein. For example, as described in U.S. Pat. No. 5,098,890, issued Mar. 24, 1992, the disclosure of which is incorporated herein by reference, oligonucleotides complementary to mRNA at or near the translation initiation codon site may be used to inhibit translation. Moreover, it has been suggested that sequences that are too distant in the 3' direction from the translation initiation site may be less effective in hybridizing the mRNA transcripts because of potential ribosomal "read-through", a phenomenon whereby the ribosome is postulated to unravel the anti-sense/sense duplex to permit translation of the message.

A variety of sequence lengths of oligonucleotide or peptide nucleic acid may be used to hybridize to mRNA transcripts. However, very short sequences (e.g., sequences containing less than 8–15 nucleobases) may bind with less specificity. Moreover, for in vivo use, short oligonucleotide sequences may be particularly susceptible to enzymatic degradation. Peptide nucleic acids, as mentioned above, likely are resistant to nuclease degradation. Where oligonucleotide and peptide nucleic acid sequences are to be provided directly to the cells, very long sequences may be less effective at inhibition because of decreased uptake by the target cell. Accordingly, where the oligonucleotide or peptide nucleic acid is to be provided directly to target cells, oligonucleotide and/or peptide nucleic acid sequences containing about 8–50 nucleobases, and more preferably 15–30 nucleobases, are envisioned to be most advantageous.

An alternative means for providing anti-sense oligonucleotide sequences to a target cell is gene therapy where, for example, a DNA sequence, preferably as part of a vector and associated with a promoter, is expressed constitutively inside the target cell. Recently, Oeller et al. (Oeller et al. (1992) *Science* 254: 437–539, the disclosure of which is incorporated herein by reference) described the in vivo inhibition of the ACC synthase enzyme using a constitutively expressible DNA sequence encoding an anti-sense sequence to the full length ACC synthase transcript. Accordingly, where the anti-sense oligonucleotide sequences are provided to a target cell indirectly, for example, as part of an expressible gene sequence to be expressed within the cell, longer oligonucleotide sequences, including sequences complementary to substantially all the protein coding sequence, may be used to advantage.

Finally, therapeutically useful oligonucleotide sequences envisioned also include not only native oligomers composed of naturally occurring nucleotides, but also those comprising modified nucleotides to, for example, improve stability and lipid solubility and thereby enhance cellular uptake. For example, it is known that enhanced lipid solubility and/or resistance to nuclease digestion results by substituting a methyl group or sulfur atom for a phosphate oxygen in the internucleotide phosphodiester linkage. Phosphorothioates ("S-oligonucleotides" wherein a phosphate oxygen is replaced by a sulfur atom), in particular, are stable to nuclease cleavage, are soluble in lipids, and are preferred, particularly for direct oligonucleotide administration. S-oligonucleotides may be synthesized chemically using conventional synthesis methodologies well known and thoroughly described in the art.

Preferred synthetic internucleoside linkages include phosphorothioates, alkylphosphonates, phosphorodithioates, phosphate esters, alkylphosphonothioates, phosphoramidates, carbamates, carbonates, phosphate triesters, acetamidate, and carboxymethyl esters. Furthermore, one or more of the 5'–3' phosphate group may be covalently joined to a low molecular weight (e.g., 15–500 Da) organic group, including, for example, lower alkyl chains or aliphatic groups (e.g., methyl, ethyl, propyl, butyl), substituted alkyl and aliphatic groups (e.g., aminoethyl, aminopropyl, aminohydroxyethyl, aminohydroxypropyl), small saccharides or glycosyl groups. Other low molecular weight organic modifications include additions to the internucleoside phosphate linkages such as cholesteryl or diamine compounds with varying numbers of carbon residues between the amino groups and terminal ribose. Oligonucleotides with these linkages or with other modifications can be prepared using methods well known in the art (see, for example, U.S. Pat. No. 5,149,798).

Suitable oligonucleotide and or peptide nucleic acid sequences which inhibit transcription and/or translation of the marker proteins can be identified using standard in vivo assays well characterized in the art. Preferably, a range of doses is used to determine effective concentrations for inhibition as well as specificity of hybridization. For example, in the cases of an oligonucleotide, a dose range of 0–100 μg oligonucleotide/ml may be assayed. Further, the oligonucleotides may be provided to the cells in a single transfection, or as part of a series of transfections. Anti-sense efficacy may be determined by assaying a change in cell proliferation over time following transfection, using standard cell counting methodology and/or by assaying for reduced expression of marker protein, e.g., by immunofluorescence. Alternatively, the ability of cells to take up and use thymidine is another standard means of assaying for cell division and may be used here, e.g., using $^3$H thymidine. Effective anti-sense inhibition should inhibit cell division sufficiently to reduce thymidine uptake, inhibit cell proliferation, and/or reduce detectable levels of marker proteins.

It is anticipated that therapeutically effective oligonucleotide or peptide nucleic acid concentrations may vary according to the nature and extent of the neoplasm, the particular nucleobase sequence used, the relative sensitivity of the neoplasm to the oligonucleotide or peptide nucleic acid sequence, and other factors. Useful ranges for a given cell type and oligonucleotide and/or peptide nucleic acid may be determined by performing standard dose range experiments. Dose range experiments also may be performed to assess toxicity levels for normal and malignant cells. It is contemplated that useful concentrations may range from about 1 to 100 μg/ml per $10^5$ cells.

For in vivo use, the anti-sense oligonucleotide or peptide nucleic acid sequences may be combined with a pharmaceutical carrier, such as a suitable liquid vehicle or excipient, and optionally an auxiliary additive or additives. Liquid vehicles and excipients are conventional and are available commercially. Illustrative thereof are distilled water, physiological saline, aqueous solutions of dextrose, and the like. For in vivo cancer therapies, the anti-sense sequences preferably can be provided directly to malignant cells, for example, by injection directly into the tumor. Alternatively, the oligonucleotide or peptide nucleic acid may be administered systemically, provided that the anti-sense sequence is associated with means for directing the sequences to the target malignant cells.

In addition to administration with conventional carriers, the anti-sense oligonucleotide or peptide nucleic acid sequences may be administered by a variety of specialized oligonucleotide delivery techniques. For example, oligonucleotides may be encapsulated in liposomes, as described in Mannino et al. (1988) *BioTechnology* 6: 682, and Felgner et al. (1989) *Bethesda Res. Lab. Focus* 11:21. Lipids useful in producing liposomal formulations include, without limitation, monoglycerides, diglycerides, sulfatides, lysolecithin, phospholipids, saponin, bile acids, and the like. Preparation of such liposomal formulations is within the level of skill in the art (see, for example, in U.S. Pat. No. 4,235,871; U.S. Pat. No. 4,501,728; U.S. Pat. No. 4,837,028; and U.S. Pat. No. 4,737,323). The pharmaceutical composition of the invention may further include compounds such as cyclodextrins and the like which enhance delivery of oligonucleotides into cells. When the composition is not administered systemically but, rather, is injected at the site of the target cells, cationic detergents (e.g. Lipofectin) may be added to enhance uptake. In addition, reconstituted virus envelopes have been successfully used to deliver RNA and DNA to cells (see, for example, Arad et al. (1986) *Biochem. Biophy. Acta.* 859: 88–94).

For therapeutic use in vivo, the anti-sense oligonucleotide and/or peptide nucleic acid sequences are administered to the individual in a therapeutically effective amount, for example, an amount sufficient to reduce or inhibit target protein expression in malignant cells. The actual dosage administered may take into account whether the nature of the treatment is prophylactic or therapeutic in nature, the age, weight, health of the patient, the route of administration, the size and nature of the malignancy, as well as other factors. The daily dosage may range from about 0.01 to 1,000 mg per day. Greater or lesser amounts of oligonucleotide or peptide nucleic acid sequences may be administered, as required. As will be appreciated by those skilled in the medical art, particularly the chemotherapeutic art, appropriate dose ranges for in vivo administration would be routine experimentation for a clinician. As a preliminary guideline, effective concentrations for in vitro inhibition of the target molecule may be determined first.

4.B. Binding Protein-based Therapeutics

As mentioned above, a cancer marker protein or a protein that interacts with the cancer marker protein may be used as a target for chemotherapy. For example, a binding protein designed to bind the marker protein essentially irreversibly can be provided to the malignant cells, for example, by association with a ligand specific for the cell and known to be absorbed by the cell. Means for targeting molecules to particular cells and cell types are well described in the chemotherapeutic art.

Binding proteins maybe obtained and tested using technologies well known in the art. For example, the binding portions of antibodies maybe used to advantage. It is contemplated, however, that intact antibodies or BABS, which preferably, have been humanized may be used in the practice of the invention. As used herein, the term "humanized" is understood to mean a process whereby the framework region sequences of a non-human immunoglobulin variable region are replaced by human variable region sequences. Accordingly, it is contemplated that such humanized binding proteins will elicit a weaker immune response than their unhumanized counterparts. Particularly useful are binding proteins identified with high affinity for the target protein, e.g., greater than about $10^9 M^{-1}$. Alternatively, DNA encoding the binding protein may be provided to the target cell as part of an expressible gene to be expressed within the cell following the procedures used for gene therapy protocols well described in the art. See, for example, U.S. Pat. No. 4,497,796, and "*Gene Transfer*", Vijay R. Baichwal, ed., (1986). It is anticipated that, once bound by binding protein, the target protein the will be inactivated or its biological activity reduced thereby inhibiting or retarding cell division.

As described above, suitable binding proteins for in vivo use, may be combined with a suitable pharmaceutical carrier, such as physiological saline or other useful carriers well characterized in the medical art. The pharmaceutical compositions may be provided directly to malignant cells, for example, by direct injection, or may be provided systemically, provided the binding protein is associated with means for targeting the protein to target cells. Finally, suitable dose ranges and cell toxicity levels may be assessed using standard dose range experiments. Therapeutically effective concentrations may range from about 0.01 to about 1,000 mg per day. As described above, actual dosages administered may vary depending, for example, on the nature of the malignancy, the age, weight and health of the individual, as well as other factors.

4.C. Small Molecule-based Therapeutics

After having isolating cervical cancer-associated nuclear matrix proteins, the skilled artisan can, using methodologies well known in the art, can screen small molecule libraries (either peptide or non-peptide based libraries) to identify candidate molecules that reduce or inhibit the biological function of the cervical cancer-associated proteins. The small molecules preferably accomplish this function by reducing the in vivo expression of the target molecule, or by interacting with the target molecule thereby to inhibit either the biological activity of the target molecule or an interaction between the target molecule and its in vivo binding partner.

It is contemplated that, once the candidate small molecules have been elucidated, skilled artisan may enhance the efficacy of the small molecule using rational drug design methodologies well known in the art. Alternatively, the skilled artisan may use a variety of computer programs which assist the skilled artisan to develop quantitative structure activity relationships (QSAR) which further to assist the design of additional candidate molecules de novo. Once identified, the small molecules may be produced in commercial quantities and subjected to the appropriate safety and efficacy studies.

It is contemplated that the screening assays may be automated thereby facilitating the screening of a large number of small molecules at the same time. Such automation procedures are within the level of skill in the art of drug screening and, therefore, are not discussed herein. Candidate peptide based small molecules may be produced by expression of an appropriate nucleic acid sequence in a host cell or using synthetic organic chemistries. Similarly, non-peptidyl-based small molecules may be produced using conventional synthetic organic chemistries well known in the art.

As described above, for in vivo use, the identified small molecules may be combined with a suitable pharmaceutical carrier, such as physiological saline or other useful carriers well characterized in the medical art. The pharmaceutical compositions may be provided directly to malignant cells, for example, by direct injection, or may be provided systemically, provided the binding protein is associated with means for targeting the protein to target cells. Finally, suitable dose ranges and cell toxicity levels may be assessed using standard dose range experiments. As described above, actual dosages administered may vary depending, for example, on the nature of the malignancy, the age, weight and health of the individual, as well as other factors.

4.D. Methods for Monitoring the Status of Cervical Cancer in an Individual

The progression of the cervical cancer or the therapeutic efficacy of chemotherapy may be measured using procedures well known in the art. For example, the efficacy of a particular chemotherapeutic agent can be determined by measuring the amount of a cervical cancer-associated protein released from cervical cancer cells undergoing cell death. As reported in PCT publication PCT/US92/09220, published May 13, 1993, incorporated by reference herein, soluble nuclear matrix proteins and fragments thereof are released by cells upon cell death. Such soluble nuclear matrix proteins can be quantitated in a body fluid and used to monitor the degree or rate of cell death in a tissue.

For example, the concentration of a body fluid-soluble nuclear matrix proteins or a fragment thereof released from cells is compared to standards from healthy, untreated tissue. Fluid samples are collected at discrete intervals during treatment and compared to the standard. It is contemplated that changes in the level of a body fluid soluble cervical cancer-associated protein, will be indicative of the efficacy of treatment (that is, the rate of cancer cell death). It is contemplated that the release of body fluid soluble interior nuclear matrix proteins can be measured in blood, plasma, urine, sputum, vaginal secretion, and breast exudate.

Where the assay is used to monitor tissue viability or progression of cervical cancer, the step of detecting the presence and abundance of the marker protein or its transcript in samples of interest is repeated at intervals and these values then are compared, the changes in the detected concentrations reflecting changes in the status of the tissue. For example, an increase in the level of cervical cancer-associated proteins may correlate with progression of the cervical cancer. Where the assay is used to evaluate the efficacy of a therapy, the monitoring steps occur following administration of the therapeutic agent or procedure (e.g., following administration of a chemotherapeutic agent or following radiation treatment). Similarly, a decrease in the level of cervical cancer-associated proteins may correlate a regression of the cervical cancer.

Thus, cervical cancer may be identified by the presence of cervical cancer-associated proteins as taught herein. Once identified, the cervical cancer may be treated using compounds which reduce in vivo the expression and/or biological activity of the cervical cancer-associated proteins. Furthermore, the methods provided herein can be used to monitor the progression of the disease and/or treatment of the disease. The following non limiting examples provide details of the isolation and characterization of cervical cancer-associated proteins and methods for their use in the detection of cervical cancer.

Example 1

Isolation of Cervical Cancer-Associated Nuclear Matrix Proteins From Cervical Cancer Tissue Samples and Cell Lines Cervical cancer-associated proteins were identified by comparing silver stained 2-D gel patterns of proteins isolated from normal and cancerous cervical cells.

Fresh cervical carcinoma tissue was obtained from patients undergoing hysterectomy for clinically localized (stage IB, II or III, International Federation of Gynecology and Obstetrics or FIGO classification) carcinomas of the cervix from the Instituto Nacional de Cancerologia in Mexico City, Mexico, in accordance with Scientific and Ethics Committee Review Board approval. A small number of tumor tissues were obtained under Institutional Review Board approval from the Pittsburgh Cancer Center (Pittsburgh, Pa.). Normal cervical tissue was obtained under Institutional Review Board approval from patients undergoing hysterectomy for causes unrelated to abnormal cervical histopathology, via the Cooperative Human Tissue Network (Columbus, Ohio). Clinical staging and tumor histopathology for twenty patients who provided tissue samples for use in these experiments are shown in Table 1. With the exception of one case of adenosquamous carcinoma, all of the tumors were squamous cell carcinomas. A majority of these were of the large cell non-keratinizing type. All the patients had localized disease with clinical stages ranging from IB to IIIB (Table 1).

TABLE 1

Patient Age, Clinical Staging and Histopathology.

| Case Number | Patient Age | FIGO Stage | Histopathological Diagnosis |
|---|---|---|---|
| 1 | 37 | IB | LCNKS† |
| 2 | 49 | IB | LCKS‡ |
| 3 | 32 | IB | Squamous, mod. well diff.* |
| 4 | 60 | IIA | LCNKS |
| 5 | 63 | III | Adenosquamous |
| 6 | 35 | IB | LCKS |
| 7 | 44 | IIIB | LCNKS |
| 8 | 31 | IB | Squamous, poorly diff.§ |
| 9 | 31 | IB | LCNKS |
| 10 | 38 | IIB | LCKS |
| 11 | 65 | IIB | LCNKS |
| 12 | 35 | IB | LCNKS |
| 13 | 43 | IB | LCNKS |
| 14 | 65 | III | LCNKS |
| 15 | 52 | IIB | LCKS |
| 16 | 47 | III | LCNKS |
| 17 | 33 | IB | LCNKS |
| 18 | 51 | IIIB | LCNKS |
| 19 | 45 | IIB | LCNKS |
| 20 | 39 | IIB | LCNKS |

| FIGO Stage | IB | IIA | IIB | III | IIIB |
|---|---|---|---|---|---|
| n | 9 | 1 | 5 | 3 | 2 |

†Large cell nonkeratinizing squamous cell carcinoma
‡Large cell keratinizing squamous cell carcinoma
*Squamous cell carcinoma, moderately well differentiated
§Squamous cell carcinoma, poorly differentiated Fresh tissue was obtained during surgery, placed into transport medium (RPMI 1640 supplemented with gentamicin and 10% fetal calf serum (GIBCO)), packed in ice, and shipped to Matritech, Inc. by overnight carrier. In a small number of cases where immediate shipment could not be arranged, tissues specimens were snap-frozen in liquid nitrogen and sent on dry ice to Matritech, Inc. by overnight carrier. Minimum size of tissue specimens was 0.2 gram. Diagnosis was obtained from pathology reports that accompanied each specimen.

Nuclear matrix proteins were isolated from cervical cancer tissue using a modification of the method of Fey et al. (1986) supra. Fresh cervical cancer tissue specimens, ranging in size from about 0.2 g to about 1.0 g, were obtained from 20 different patients. Tissue specimens were minced into small (1 mm$^3$) pieces and homogenized with a Teflon pestle on ice and treated with a buffered solution containing 0.5% Triton-X-100, vanadyl riboside complex (RNAase inhibitor, Five Prime-Three Prime, Inc.) plus a protease inhibitor cocktail containing phenylmethyl sulfonyl fluoride (Sigma Chemical Co.), aprotinin and leupeptin (Boehringer Mannheim), to remove lipids and soluble proteins.

Stromal aggregates were removed by filtering the homogenate through 250 micron Nitex nylon screen (Tetko, Inc.) followed by a centrifugation step (600×g, 4° C., 5 min). Soluble cytoskeletal proteins were removed by incubating the pellet in an extraction buffer containing 250 mM $(NH_4)_2SO_4$, 0.5% Triton X-100, vanadyl riboside complex and protease inhibitor cocktail on ice for 10 minutes followed by centrifugation (600×g, 4° C., 5 min).

Chromatin was removed by incubating the pellet in DNAase (100 mg/mL, Boehringer-Mannheim) in a buffered solution containing protease inhibitor cocktail for 45 minutes at 25° C. The remaining pellet fraction, which contained nuclear matrix proteins and intermediate filaments, was solubilized in disassembly buffer containing 8M urea, protease inhibitor cocktail and 1% (vol/vol) 2-mercaptoethanol. Insoluble contaminants, primarily carbohydrates and extracellular matrix were removed by ultracentrifugation (163,000×g, 20° C., 1 hr). Intermediate filaments were allowed to reassemble upon removal of urea by dialysis in an assembly buffer containing 150 mM KCl, 24 mM imidazole HCl, 5 mM $MgCl_2$, 0.125 mM EGTA and 2 mM dithiothreitol (DTT) with protease inhibitors and were removed by ultracentrifugation (109,000×g, 15° C., 1.5 hr), leaving the nuclear matrix proteins in the supernatant fraction.

In addition, cervical cancer-associated proteins were isolated from CaSki, ME-180, C33A, HeLa (S3 subline), SiHa, C4-1, C4-11, and HT-3 cervical tumor cell lines. Each cell line was obtained from the American Type Culture Collection (ATCC) and maintained at 37° C. in 5% $CO_2$ in Dulbecco's Modified Eagles Medium supplemented with 10% fetal calf serum, gentamicin, fungizone and 0.12% SeraExtend (Irvine Scientific). For nuclear matrix extraction studies, cells were grown to approximately 80% confluence in 10 stage cell culture factories (Nunc), harvested by trypsinization, counted and extracted in the same manner as homogenized tumor tissue. Protein concentration of nuclear matrix proteins was determined by the Coomassie Plus Protein Assay Kit (Pierce Chemical) using a bovine gamma globulin standard. Proteins were immediately precipitated in 80% ethanol and stored at −80° C. until use.

The resulting nuclear matrix proteins were next characterized by high-resolution two-dimensional gel electrophoresis according to the procedure of O'Farrell (1975) *J. Biol. Chem.* 250: 4007–4021 (1975), on an Investigator 2-D system (Oxford Glycosystems, Bedford, Mass.). Nuclear matrix proteins were solubilized for isoelectric focusing (IEF) analysis in sample buffer containing 9M urea, 65 mM 3-[(cholamidopropyl)dimethylamino]-1-propanesulfate (CHAPS), 2.2% ampholytes, and 140 mM dithiothreitol (DTT). Two hundred micrograms of nuclear matrix proteins were loaded per gel.

One-dimensional isoelectric focusing was carried out for 18,000 volt-hours using 1 mm×18 mm gel tubes. Following first dimension electrophoresis, gels were extruded from gel tubes, equilibrated for 2 minutes in a buffer containing 0.3M Tris base, 0.075M Tris-HCl, 3.0% SDS, 50 mM DTT, and 0.01% bromophenol blue and placed on top of 1 mm 10% Tris-glycine-SDS Duracryl (Oxford Glycosystems) high tensile strength polyacrylamide electrophoresis slab gels. Second dimension slab gels were electrophoresed at 16 Watts per gel and 12° C. constant temperature for approximately 5 hours. Molecular weight standards consisted of bovine albumin ($M_r$ 66,000), ovalbumin ($M_r$ 45,000), glyceraldehyde-3-phosphate dehydrogenase ($M_r$ 36,000), carbonic anhydrase ($M_r$ 29,000), bovine pancreatic trypsinogen ($M_r$ 24,000), and soybean trypsin inhibitor ($M_r$ 20,100) (Sigma Chemical Co.). Isoelectric points were determined using internal control proteins with well-characterized isoelectric points. Following electrophoresis, gels were fixed in a solution containing 40% ethanol/10% acetic acid followed by treatment with a solution containing 0.5% glutaraldehyde. Gels were washed extensively and silver stained according to the method of Rabillioud et al. (Rabillioud et al. (1992) *Electrophoresis* 13: 429–439) and dried between sheets of cellophane paper.

Silver-stained gels were imaged using a MasterScan Biological Imaging System (CSP, Inc., Billerica, Mass.) according to the manufacturer's instructions. Digital filtering algorithms were used to remove both uniform and non-uniform background without removing critical image data. Two-D scan (TM) two-dimensional gel analysis and database software (version 3.1) using multiple Gaussian least-squares fitting algorithms were used to compute spot patterns into optimal-fit models of the data as reported by Olson et al. (1980) *Anal. Biochem.* 169: 49–70. Triangulation from the internal standards was used to precisely determine the molecular weight and isoelectric point of each target protein of interest. Interpretive densitometry was performed using specific software application modules to integrate the data into numeric and graphical reports for each gel being analyzed.

Example 2

Figure 1B:
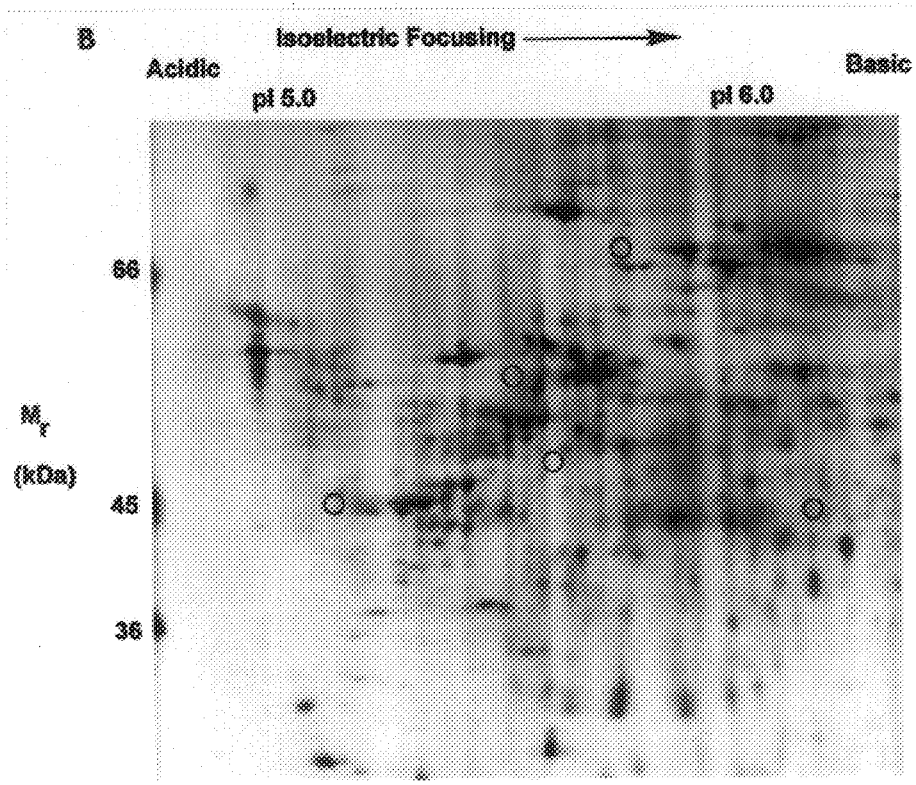
FIG. 1b is a high resolution two-dimensional gel electrophoresis pattern of nuclear matrix proteins isolated from a normal cervical tissue sample. As a reference, the relative positions corresponding to the CvC-1 to CvC-5 proteins of FIG. 1a are encircled and marked with reference numbers 1–5.

Identification of Cervical Cancer-associated Nuclear Matrix Proteins Having Differential Appearance on 2-D Gels As described in the previous Example, 2-D gel electrophoresis patterns were obtained by fractionating proteins isolated from either normal or cancerous cervical cells. FIG. 1*a* shows a typical cervical cancer-associated nuclear matrix protein pattern obtained from cervical cancer tissue. FIG. 1*b* shows a typical gel pattern produced by nuclear matrix proteins obtained from a normal cervical tissue sample. Approximately 600 proteins were resolved per gel. Most of the proteins observed were always present, irrespective of the type of cervical tissue under investigation.

Comparison of FIGS. 1 and 2 reveals that, while most proteins in the cancer and non-cancer samples are identical, there are five proteins that are unique to the cervical cancer sample (labeled in FIG. 1). The proteins, designated CvC-1 through CvC-5, were detected in 20 tissue samples obtained from patients diagnosed with cervical carcinoma but were not detected in cervical tissue isolated from a group of 10 normal individuals. Table 2 identifies proteins, designated CvC-1 through CvC-5, by their approximate molecular weight and isoelectric point. Both the molecular weight and isoelectric point values listed in Table 1 are approximate and accurate to within 2,000 Daltons for molecular weight and to within 0.2 pI units for isoelectric point. A detailed analysis to identify proteins common to normal cervical tissue but absent from cervical cancer tissue did not reveal any proteins that were specifically associated with normal cervical tissue.

TABLE 2

Cervical Cancer-associated Proteins

| Peptide | Molecular Weight | Isoelectric Point | Cervical Cancer | Normal Cervical |
|---------|------------------|-------------------|-----------------|-----------------|
| CvC-1 | 69,408 | 5.78 | + | − |
| CvC-2 | 53,752 | 5.54 | + | − |
| CvC-3 | 47,887 | 5.60 | + | − |
| CvC-4 | 46,006 | 5.07 | + | − |
| CvC-5 | 44,864 | 6.61 | + | − |

In addition, the expression of nuclear matrix proteins isolated from cervical cancer cell lines was investigated, the results of which are summarized in Table 3, below. It is known that tumors of epithelial cell origin are characterized by the presence of stroma and other elements, such as those resulting from infiltrating inflammatory cells. Detection of nuclear matrix or matrix-associated proteins in tumor cell lines derived from cervical epithelial cell tumors reduces the possibility that the proteins are the result of stromal or other types of contamination of the nuclear matrix preparation.

Figure 2A:
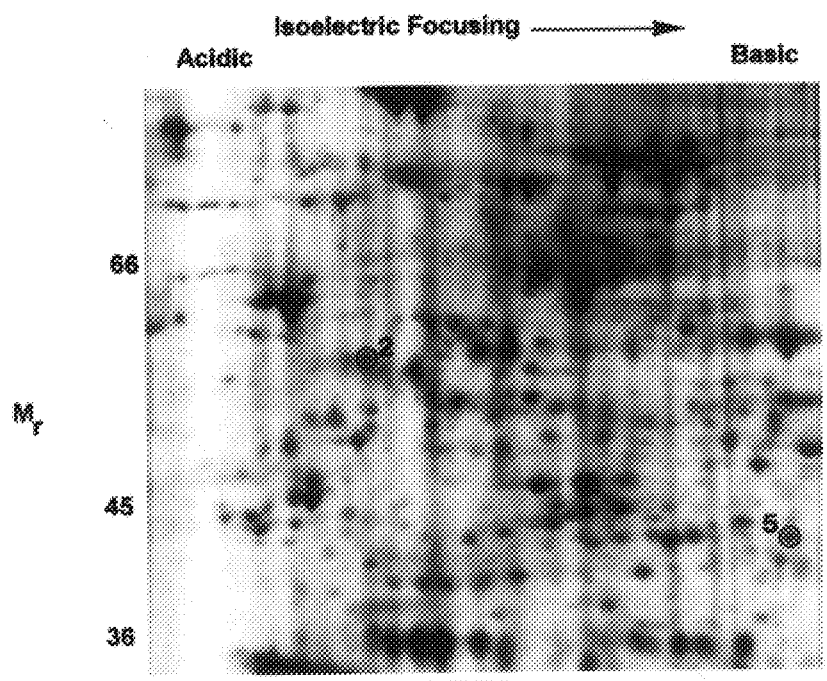
FIG. 2a is a high resolution two-dimensional gel electrophoresis pattern of nuclear matrix proteins isolated from the cervical carcinoma-derived cell line C33A. Tumor-associated proteins CvC-2 and CvC-5 are encircled and marked with reference numbers 2 and 5.
Figure 2B:
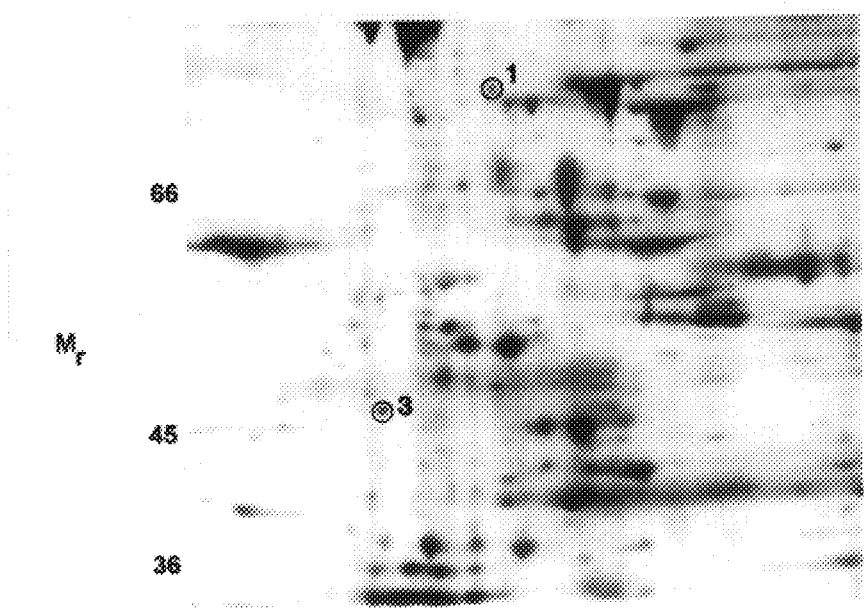
FIG. 2b is a high resolution two-dimensional gel electrophoresis pattern of nuclear matrix proteins isolated from CaSki cells. Tumor-associated proteins CvC-1 and CvC-3 are encircled and marked with reference numbers 1 and 3.

2-D gel electrophoresis patterns were obtained from samples containing cervical cancer cells derived from cervical cancer cell lines. FIG. 2*a* shows a cervical cancer-associated nuclear matrix protein pattern obtained from the cervical cancer cell line C33A. In FIG. 2*a*, tumor-associated proteins CvC-2 and CvC-5 are encircled and identified with numbers 2 and 5. FIG. 2*b* shows a gel pattern produced by nuclear matrix proteins obtained from the cervical cancer cell line CaSki a normal cervical tissue sample. In FIG. 2*b*, tumor associated proteins CvC-1 and CvC-3 are encircled and identified with numbers 1 and 3.

Four of the five tumor-associated proteins (CvC1 to CvC-3 and CvC-5) were reproducibly detected in one or more cervical tumor cell lines (FIG. 2, Table 3), confirming the epithelial origin of the proteins. Expression of the fifth protein, CvC-4, was variable but could be detected in the C33A tumor cell line (Table 3).

TABLE 3

Cervical Carcinoma-associated Protein Expression in Cervical Tumor Cell Lines.

| Tumor cell line | Histopathology of tumor or origin | Nuclear matrix proteins expressed* | | | | |
|---|---|---|---|---|---|---|
| | | CvC-1 | CvC-2 | CvC-3 | CvC-4 | CvC-5 |
| CaSKI† | Epidermoid | + | tr‡ | + | − | + |
| SiHa | Squamous cell | − | tr | +++ | − | + |
| HeLa | Adeno-carcinoma | tr | − | +++ | − | + |
| ME-180† | Epidermoid | − | tr | + | − | + |
| C33A⁻ | Squamous cell | + | ++ | − | var§ | + |
| C4-I | Squamous cell | tr | − | +++ | − | + |
| C4-II | Squamous cell | − | − | − | − | tr |
| HT-3† | Epidermoid | tr | − | + | − | tr |

*Nuclear matrix proteins were extracted from tumor cell lines obtained from the American Type Culture Collection using Fey and Penman extraction methodology.

TABLE 3-continued

Cervical Carcinoma-associated Protein Expression in Cervical Tumor Cell Lines.

| Tumor cell line | Histo-pathology of tumor or origin | Nuclear matrix proteins expressed* | | | | |
|---|---|---|---|---|---|---|
| | | CvC-1 | CvC-2 | CvC-3 | CvC-4 | CvC-5 |

†Tumor cell lines arising from metastatic epidermoid carcinoma originating from cervix.
‡Indicates low level expression, detected by silver stain.
§Indicates variable expression, detected by silver stain.

Two of the cervical cancer-associated proteins specific to cervical cancer cells were isolated and processed for microsequence analysis.

Example 3

Characterization of Cervical Cancer-Associated Nuclear Matrix Protein Markers Two protein staining spots detectable on a 2-D gel corresponding to CvC-3 and CvC-5 were isolated, the protein harvested and subjected to microsequence analysis, as described hereinbelow.

For sequencing of the cervical cancer-associated polypeptides CvC-3 and CvC-5, the nuclear matrix fraction from HeLa cells were electrophoresed on two-dimensional gels as described above. Each gel was loaded with 300 micrograms of protein isolated by the nuclear matrix protein isolation procedure, as described above. Following the second-dimension of electrophoresis, proteins were visualized by reverse staining. Briefly, gels were soaked in 200 mM imidazole for 10 minutes, rinsed for 1 minute in water, followed by 1–2 minutes in 300 mM zinc chloride (Fernandez-Patron et al. (1992) BioTechniques 12: 564–573). After the protein-containing spots began to appear, the gels were placed in water, and the relevant gels spots excised. The isolated gel spots representing individual cervical cancer-associated polypeptides were pooled and destained by a 5 minute wash in 2% citric acid, followed by several washes in 100 mM Tris hydrochloride at pH 7.0 to raise the pH within the gel pieces.

Each set of pooled gel fragments was then diluted with an equal volume of 2× sodium dodecyl sulfate polyacrylamide gel electrophoresis (SDS-PAGE) sample buffer (250 mM Tris-Cl, 2% SDS, 20% glycerol, 0.01% bromophenol blue and 10% β-mercaptoethanol, pH 6.8) and incubated at 75° C. for 3 minutes. The gel fragment-containing samples were then cooled on ice and loaded onto a 4% polyacrylamide stacking/11% polyacrylamide separating SDS-PAGE gel, and electrophoresed in 1× Tank Buffer (24 mM Tris-HCl, 192 mM glycine, 1% SDS, pH 8.3) to focus the gel spots into bands. Molecular weight markers (BioRad #161–0304) were used on each gel to relate the observed molecular weights on the one-and two-dimensional gels. Following electrophoresis, these gels were electroblotted onto Immobilon PVDF membranes (Oxford Glycosystems, Inc.) (Towbin et al. (1979) Proc. Nat'l. Acad. Sci. USA 76: 4350–4354) as modified by Matsudaira (Matsudaira et al. (1987) J. Biol. Chem. 262: 10035) for the mini-gel format. The membranes were then stained for 1 minute with Buffalo Black (0.1% in 1% acetic acid, 40% methanol) and rinsed with water. Regions of membrane containing polypeptide bands were excised with a clean scalpel.

The PVDF-bound polypeptides were then subjected to tryptic peptide mapping and microsequencing (Fernandez et al. (1994) Analytical Biochem. 218: 112–117) at the Microchemistry Facility at the Worcester Foundation for Biomedical Research using a Hewlett Packard Model 1090M HPLC. Sequence determinations were made on an Applied Biosystems ProCise Sequenator, and most were confirmed by MALDI-TOF mass spectrometry of individual peptides. Other peptides were identified by mass analysis alone, or mass analysis of carboxypeptidase-digested material.

Microsequence Analysis of CvC-3 Peptides

Using the methodology described above, CvC-3 was isolated from approximately 120 two-dimensional gels of HeLa nuclear matrix and refocused on Immobilon-PVDF membrane for microsequence analysis. Although only one protein was observed by silver staining the 2-D gel location identified as CvC-3, refocusing of the protein on a one dimensional 11% minigel resulted in the resolution of two clearly separable protein bands. These proteins were labeled as CvC-3H and CvC-3L and submitted separately for microsequence analysis. Analysis of the tryptic maps indicates that two different proteins were contained in the two bands seen on the refocusing minigel, since little overlap was observed in the peak retention times of the two peptides.

Ten masses were detected by mass spectrometry from seven of the CvC-3H peaks. Amino acid sequence was obtained for three peptides, two by Edman degradation and one by carboxypeptidase-MALDI-TOF analysis. The sequences obtained for these peptides, shown in Table 4 match a protein known as IEF SSP 9502 or "novel human nuclear phosphoprotein". (Honore et. al. (1994) supra; GenBank Accession #LO7758). The complete amino acid sequence for this protein, as derived from a gene sequence, is shown in SEQ. ID No.: 10. Seven other masses from peak fractions separated on the CvC-3H tryptic map also matched those of predicted tryptic fragments from this protein. Mass correlation data of tryptic peptides from CvC-3H are summarized in Table 4. The predicted molecular weight of the nuclear phosphoprotein, based upon its nucleotide sequence is 55 kDa, whereas its observed molecular weight by 2-D gel analysis is 79 kDa (Honore et al. (1994) supra).

TABLE 4

Mass Correlation of CvC-3H-derived Tryptic Peptides

| Peak | Observed Mass (Da) | Predicted Mass (Da) | Delta | Sequence | SEQ. ID. No. | Protein |
|---|---|---|---|---|---|---|
| 4 | 1110.64 | 1109.25 | 0.13% | PAASLAVHTDK | 1 | IEF SSP 9502 |
| 5 | 834.62 | 835.92 | 0.16% | FSGQIER | 2 | IEF SSP 9502 |
| 7 | 1056.57 | 1057.26 | 0.07% | RLIAEAKEK | 3 | IEF SSP 9502 |
| 8 | 1187.45 | 1185.37 | 0.18% | PSLVHSRDM | 4 | IEF SSP 9502 |
| 10 | 1774.73 | 1766.93 | 0.44% | VWDISTVSSVNEAFGR* | 5 | IEF SSP 9502 |
| 10 | 1802.22 | 1805.02 | 0.16% | LVLGSARNSSISGPFGSR | 6 | IEF SSP 9502 |
| 11 | 2746.27 | 2743.02 | 0.12% | SDKPIFTLNAHNDEISGLDLSSQIK** | 7 | IEF SSP 9502 |
| 12 | 2412.23 | 2409.68 | 0.11% | VQTLQFHPFEAQTLISGSYDK* | 8 | IEF SSP 9502 |
| 12 | 2475.13 | 2483.98 | 0.36% | MGVLFCSSCCPDLPFIYAFGGQK | 9 | IEF SSP 9502 |

*Underlining reflects sequences confirmed by Edman degradation.
**Bolded underlining reflects sequence confirmed by carboxypeptidase digestion.

In addition, seven masses were detected by mass spectrometry from four peaks derived from tryptic digestion of CvC-3L. One of these was directly sequenced and was found to be identical to cytokeratin 17 (Troyanovsky et al. (1992), supra; GenBank Accession #Q04695). Six other masses from fractions separated on the CvC-3L tryptic map also matched those of predicted tryptic fragments of human cytokeratin 17. The amino acid sequence for this protein, from Troyanovsky et al. (1992), supra, is shown in SEQ. ID No.: 18. Mass correlation data of tryptic peptides from CvC-3L are summarized in Table 5. The apparent molecular weight of CvC-3L (47.9 kDa) is consistent with the detection of a full length molecule of cytokeratin 17 (predicted molecular weight, 48 kDa) in cervical tumors.

defined by CvC-5 (Table 3). Without wishing to be bound by theory, one explanation for the apparent detection of only one protein in the CvC-5 gel spot in many tumors is that one of the proteins may be more abundant, thereby masking the presence of other closely migrating proteins. When CvC-5 gel spots were pooled and refocused onto a one dimensional minigel, only one diffusely stained protein band was detected.

The tryptic map of the diffuse band containing the polypeptide components of the CvC-5 gel spot contained approximately 30 resolved peaks. Mass analysis was performed on 12 of these peaks and 30 masses were obtained. Six amino acid sequences were obtained by automated Edman degradation, revealing the presence of three distinct

TABLE 5

Mass Correlation of CvC-3L-derived Tryptic Peptides.

| Peak | Observed Mass (Da) | Predicted Mass (Da) | Delta | Sequence | SEQ. ID No. | Protein |
|---|---|---|---|---|---|---|
| 4 | 995.46 | 994.03 | 0.14% | DYSQYYR | 11 | Cytokeratin 17 |
| 4 | 1244.97 | 1242.34 | 0.21% | NHEEEMNALR | 12 | Cytokeratin 17 |
| 9 | 1518.03 | 1516.67 | 0.09% | LLEGEDAHLTQYK* | 13 | Cytokeratin 17 |
| 10 | 791.19 | 790.94 | 0.03% | ILNEMR | 14 | Cytokeratin 17 |
| 10 | 835.16 | 832.91 | 0.27% | SEISELR | 15 | Cytokeratin 17 |
| 12 | 1144.21 | 1144.21 | 0.00% | DAEDWFFSK | 16 | Cytokeratin 17 |
| 12 | 1187.57 | 1186.33 | 0.10% | LSVEADINGLR | 17 | Cytokeratin 17 |

*Underlining reflects sequences confirmed by Edman degradation.

Microsequence Analysis of CvC-5 Peptides

The gel spot identified as CvC-5 was collected from HeLa nuclear matrix from the same preparative two-dimensional gels that were used for the collection of CvC-3. Approximately 100 gel spots were collected as described and refocused on Immobilon-PVDF membrane for microsequence analysis. During the initial identification of tumor associated proteins it was noted that in some cervical tumors, two proteins appeared to migrate very closing together in the location identified as CvC-5. Only one protein was clearly apparent. However, when the expression of this protein was examined in cervical tumor cell lines, 3 of 8 cell lines showed the presence of at least two proteins in the area polypeptides. The first of these is a protein known as TDP-43 or TAR DNA binding protein (Out et. al. (1995) supra; GenBank Accession #U23731). The complete amino acid sequence, as derived from the gene sequence for this protein, is shown in SEQ. ID. No. 26. The apparent molecular weight of 43 kDa suggests identification of the intact protein in cervical tumors. Six other masses from fractions separated on the CvC-5 tryptic map also matched those of predicted tryptic fragments from this protein. Mass correlation data and peptide sequence data of tryptic peptides matching TDP-43 are shown in Table 6.

TABLE 6

Mass Correlation of CvC-5 Derived Tryptic Peptides.

| Peak | Observed Mass (Da) | Predicted Mass (Da) | Delta | Sequence | SEQ. ID. No. | Protein |
|---|---|---|---|---|---|---|
| 12 | 1729.01 | 1726.79 | 0.13% | FGGNPGGFGNQGGFGNSR | 19 | TDP43 |
| 13 | 655.72 | 653.78 | 0.30% | WCDCK | 20 | TDP43 |
| 13 | 834.24 | 833.89 | 0.04% | TTEQDLK | 21 | TDP43 |
| 14 | 682.63 | 681.79 | 0.12% | GFGFVR | 22 | TDP43 |
| 16 | 1511.88 | 1511.66 | 0.01% | LPNSKQSQDEPLR | 23 | TDP43 |
| 21 | 1280.01 | 1281.41 | 0.11% | KMDETDASSAVK | 24 | TDP43 |
| 25 | 1342.84 | 1341.61 | 0.09% | TSDLIVLGLPWK* | 25 | TDP43 |

*Underlining reflects sequences confirmed by Edman degradation.

Sequence information obtained for three peptides matched a nuclear pore protein known as nucleoporin or Nup358 (Wu el. al (1995) supra, Gen Bank Accession #L41840). The complete amino acid sequence, as derived from the gene sequence, is shown in SEQ. ID. No.:34. Mass correlation data for five additional masses identified from the CvC-5 tryptic map which matched predicted tryptic fragments of Nup358 are shown in Table 7. The location of the sequences matching Nup358 suggests our isolation of a C-terminal fragment of the intact protein ($M_r$ 358 kDa) from cervical tumors.

The third polypeptide identified in the CvC-5 gel spot is a fragment of lamin A (Fisher et. al. (1986), supra; GenBank Accession #M13452). Two sequences matching lamin A were obtained by Edman degradation (Table 8). Nine additional masses from fragments of the CvC-5 tryptic map match predicted masses of tryptic fragments from lamin A. Mass correlation data for these additional masses were shown in Table 8. The amino acid sequence for this protein, (Fisher et. al. (1986) supra), is shown in SEQ. ID No.: 46.

TABLE 7

Mass Correlation of CvC-5 Derived Tryptic Peptides.

| Peak | Observed Mass (Da) | Predicted Mass (Da) | Delta | Sequence | SEQ. ID No. | Protein |
|---|---|---|---|---|---|---|
| 9 | 613.14 | 614.66 | 0.25% | NYYR* | 27 | nup358 |
| 10 | 613.20 | 614.66 | 0.24% | NYYR* | 28 | nup358 |
| 11 | 702.22 | 701.78 | 0.06% | VQEAQK | 29 | nup358 |
| 16 | 938.37 | 939.10 | 0.08% | EVADCFK | 30 | nup358 |
| 17 | 2459.64 | 2458.54 | 0.04% | HDGTGGQSIYGDKFEDENFDVK** | 31 | nup358 |
| 21 | 1419.00 | 1419.71 | 0.05% | ITMELFXNIVPR** | 32 | nup358 |
| 21 | 2773.58 | 2771.11 | 0.09% | HTGPGLLSMANQGQNTNNXXFVIXLK** | 33 | nup358 |

*Denotes a peptide that appeared in two adjacent HPLC fractions
**Underlining reflects sequences confirmed by Edman degradation

TABLE 8

Mass Correlation of CvC-5 derived Tryptic Peptides.

| Peak | Observed Mass (Da) | Predicted Mass (Da) | Delta | Sequence | Seq. ID No. | Protein |
|---|---|---|---|---|---|---|
| 7 | 667.10 | 666.69 | 0.06% | EFESR | 35 | lamin A |
| 8 | 569.50 | 568.63 | 0.15% | TYSAK* | 36 | lamin A |
| 8 | 585.78 | 587.63 | 0.31% | LDNAR | 37 | lamin A |
| 11 | 569.10 | 568.63 | 0.08% | TYSAK* | 38 | lamin A |
| 11 | 1025.18 | 1023.11 | 0.20% | NIYSEELR | 39 | lamin A |
| 12 | 805.83 | 803.91 | 0.24% | TALSEKR | 40 | lamin A |
| 17 | 1349.52 | 1347.56 | 0.15% | LALDMEIHAYR** | 41 | lamin A |
| 17 | 1009.78 | 1009.18 | 0.06% | EMAEMRAR | 42 | lamin A |
| 21 | 1912.74 | 1913.07 | 0.02% | EELDFQKNIYSEELR* | 43 | lamin A |
| 22 | 1896.58 | 1894.13 | 0.13% | MQQQLDEYQELLDIK** | 44 | lamin A |
| 22 | 1913.03 | 1913.07 | 0.00% | EELDFQKNIYSEELR* | 45 | lamin A |

*Denotes a peptide that appeared in two adjacent HPLC fractions
**Underlining reflects sequences confirmed by Edman degradation Cervical cancer-associated proteins may be identified using well-known techniques based upon the partial amino acid sequences provided above. Thus, the cervical cancer-associated proteins detected according to methods of the invention may be referred to as comprising a continuous sequence shown in the above-noted sequence fragments. It is appreciated that the skilled artisan, in view of the foregoing disclosure, would be able to produce an antibody directed against any cervical cancer-associated protein identified by the methods described herein. Moreover, the skilled artisan, in view of the foregoing disclosure, would be able to produce nucleic acid sequences which encode the fragments described above, as well as nucleic acid sequences complementary thereto. In addition, the skilled artisan using conventional recombinant DNA methodologies, for example, by screening a cDNA library with such a nucleic acid sequence, would be able to isolate full length nucleic acid sequences encoding target cervical cancer-associated proteins. Such full length nucleic acid sequences, or fragments thereof, may be used to generate nucleic acid-based detection systems or therapeutics.

Example 4

Production of Antibodies Which Bind Specifically to Cervical Cancer-associated Proteins Once identified, a cervical cancer-associated protein, such as a CvC-1 through CvC-5, may be detected in a tissue or body fluid sample using numerous binding assays that are well known to those of ordinary skill in the art. For example, as discussed above, a cervical cancer-associated protein may be detected in either a tissue or body fluid sample using an antibody, for example, a monoclonal antibody, which bind specifically to an epitope disposed upon the cervical cancer-associated protein. In such detection systems, the antibody preferably is labeled with a detectable moiety.

Provided below is an exemplary protocol for the production of an anti-cervical cancer-associated monoclonal antibody. Other protocols also are envisioned. Accordingly, the particular method of producing antibodies to target proteins is not envisioned to be an aspect of the invention.

Balb/c by J mice (Jackson Laboratory, Bar Harbor, Me.) are injected intraperitoneally with the target protein, e.g., CvC-3 protein isolated from HeLa cell nuclear matrix, every 2 weeks until the immunized mice obtain the appropriate serum titer. Thereafter, the mice are injected with 3 consecutive intravenous boosts. Freund's complete adjuvant (Gibco, Grand Island) is used in the first injection, incomplete Freund's in the second injection; and saline is used for subsequent intravenous injections. The animal is then sacrificed and its spleen removed. Spleen cells (or lymph node cells) then are fused with a mouse myeloma line, e.g., using the method of Kohler el al. (1975) *Nature* 256: 495, the disclosure of which is incorporated herein by reference. Hybridomas producing antibodies that react with the target proteins then are cloned and grown as ascites. Hybridomas are screened by nuclear reactivity against the cell line that is the source of the immunogen, and by tissue immunohistochemistry using standard procedures known in the immunology art. Detailed descriptions of screening protocols, ascites production and immunoassays also are disclosed in PCT/US92/09220 published May 13, 1993, the disclosure of which is incorporated herein by reference.

Example 5

Antibody-based Assay for Detecting Cervical Cancer in an Individual

The following assay has been developed for tissue samples, however, it is contemplated that similar assays for testing fluid samples may be developed without undue experimentation. A typical assay may employ a commercial immunodetection kit, for example, the ABC Elite Kit from Vector Laboratories, Inc.

A biopsy sample, for example, a Pap smear is removed from the patient under investigation in accordance with the appropriate medical guidelines. The sample then is applied to a glass microscope slide and the sample fixed in cold acetone for 10 minutes. Then, the slide is rinsed in distilled water and pretreated with a hydrogen peroxide containing solution (2 mL 30% $H_2O_2$ and 30 mL cold methanol). The slide is then rinsed in a Buffer A comprising Tris Buffered Saline (TBS) with 0.1% Tween and 0.1% Brij. A mouse anti-cervical cancer-associated protein monoclonal antibody in Buffer A is added to the slide and the slide then incubated for one hour at room temperature. The slide is then washed with Buffer A, and a secondary antibody (ABC Elite Kit, Vector Labs, Inc) in Buffer A is added to the slide. The slide is then incubated for 15 minutes at 37° C. in a humidity chamber. The slides are washed again with Buffer A, and the ABC reagent (ABC Elite Kit, Vector Labs, Inc.) is then added to the slide for amplification of the signal. The slide is then incubated for a further 15 minutes at 37° C. in the humidity chamber.

The slide then is washed in distilled water, and a diamino benzenedine (DAB) substrate added to the slide for 4–5 minutes. The slide is then rinsed with distilled water, counterstained with hematoxylin, rinsed with 95% ethanol, rinsed with 100% ethanol, and then rinsed with xylene. A cover slip is then applied to the slide and the result observed by light microscopy.

Equivalents

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

SEQUENCE LISTING ( 1 ) GENERAL INFORMATION:

( i i i ) NUMBER OF SEQUENCES: 46

( 2 ) INFORMATION FOR SEQ ID NO:1:

( i ) SEQUENCE CHARACTERISTICS:
        ( A ) LENGTH: 11 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:1:

```
Pro  Ala  Ala  Ser  Leu  Ala  Val  His  Thr  Asp  Lys
 1               5                        10
```

( 2 ) INFORMATION FOR SEQ ID NO:2:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:2:

```
Phe  Ser  Gly  Gln  Ile  Glu  Arg
 1               5
```

( 2 ) INFORMATION FOR SEQ ID NO:3:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:3:

```
Arg  Leu  Ile  Ala  Glu  Ala  Lys  Glu  Lys
 1               5
```

( 2 ) INFORMATION FOR SEQ ID NO:4:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:4:

```
Pro  Ser  Leu  Val  His  Ser  Arg  Asp  Met
 1               5
```

( 2 ) INFORMATION FOR SEQ ID NO:5:

( i ) SEQUENCE CHARACTERISTICS:
        ( A ) LENGTH: 16 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:5:

```
Val  Trp  Asp  Ile  Ser  Thr  Val  Ser  Ser  Val  Asn  Glu  Ala  Phe  Gly  Arg
 1               5                        10                       15
```

(2) INFORMATION FOR SEQ ID NO:6:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:6:

```
Leu  Val  Leu  Gly  Ser  Ala  Arg  Asn  Ser  Ser  Ile  Ser  Gly  Pro  Phe  Gly
 1                    5                           10                          15

Ser  Arg
```

(2) INFORMATION FOR SEQ ID NO:7:

(i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:7:

```
Ser  Asp  Lys  Pro  Ile  Phe  Thr  Leu  Asn  Ala  His  Asn  Asp  Glu  Ile  Ser
 1                    5                           10                          15

Gly  Leu  Asp  Leu  Ser  Ser  Gln  Ile  Lys
                20                       25
```

(2) INFORMATION FOR SEQ ID NO:8:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:8:

```
Val  Gln  Thr  Leu  Gln  Phe  His  Pro  Phe  Glu  Ala  Gln  Thr  Leu  Ile  Ser
 1                    5                           10                          15

Gly  Ser  Tyr  Asp  Lys
                20
```

(2) INFORMATION FOR SEQ ID NO:9:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:9:

```
Met  Gly  Val  Leu  Phe  Cys  Ser  Ser  Cys  Cys  Pro  Asp  Leu  Pro  Phe  Ile
 1                    5                           10                          15

Tyr  Ala  Phe  Gly  Gly  Gln  Lys
                20
```

(2) INFORMATION FOR SEQ ID NO:10:

(i) SEQUENCE CHARACTERISTICS:
        (A) LENGTH: 501 amino acids
        (B) TYPE: amino acid ( C ) STRANDEDNESS:
( D ) TOPOLOGY: linear ( i i ) MOLECULE TYPE: peptide ( x i ) SEQUENCE DESCRIPTION: SEQ ID NO:10:

| Met | Asn | Arg | Ser | Arg | Gln | Val | Thr | Cys | Val | Ala | Trp | Val | Arg | Cys | Gly |
|---|---|---|---|---|---|---|---|---|---|---|---|---|---|---|---|
| 1 | | | | 5 | | | | | 10 | | | | | 15 | |
| Val | Ala | Lys | Glu | Thr | Pro | Asp | Lys | Val | Glu | Leu | Ser | Lys | Glu | Val | Val |
| | | | | 20 | | | | | 25 | | | | | 30 | |
| Lys | Arg | Leu | Ile | Ala | Glu | Ala | Lys | Glu | Lys | Leu | Gln | Glu | Gly | Gly | Gly |
| | | | 35 | | | | | 40 | | | | | 45 | | |
| Gly | Ser | Asp | Glu | Glu | Glu | Thr | Gly | Ser | Pro | Ser | Glu | Asp | Gly | Met | Gln |
| | | 50 | | | | | 55 | | | | | 60 | | | |
| Ser | Ala | Arg | Thr | Gln | Ala | Arg | Pro | Arg | Glu | Pro | Leu | Glu | Asp | Gly | Asp |
| 65 | | | | | 70 | | | | | 75 | | | | | 80 |
| Pro | Glu | Asp | Asp | Arg | Thr | Leu | Asp | Asp | Glu | Leu | Ala | Glu | Tyr | Asp | |
| | | | | 85 | | | | | 90 | | | | | 95 | |
| Leu | Asp | Lys | Tyr | Asp | Glu | Glu | Gly | Asp | Pro | Asp | Ala | Glu | Thr | Leu | Gly |
| | | | | 100 | | | | | 105 | | | | | 110 | |
| Glu | Ser | Leu | Leu | Gly | Leu | Thr | Val | Tyr | Gly | Ser | Asn | Asp | Gln | Asp | Pro |
| | | | 115 | | | | | 120 | | | | | 125 | | |
| Tyr | Val | Thr | Leu | Lys | Asp | Thr | Glu | Gln | Tyr | Glu | Arg | Glu | Asp | Phe | Leu |
| | | 130 | | | | | 135 | | | | | 140 | | | |
| Ile | Lys | Pro | Ser | Asp | Asn | Leu | Ile | Val | Cys | Gly | Arg | Ala | Glu | Gln | Asp |
| 145 | | | | | 150 | | | | | 155 | | | | | 160 |
| Gln | Cys | Asn | Leu | Glu | Val | His | Val | Tyr | Asn | Gln | Glu | Glu | Asp | Ser | Phe |
| | | | | 165 | | | | | 170 | | | | | 175 | |
| Tyr | Val | His | His | Asp | Ile | Leu | Leu | Ser | Ala | Tyr | Pro | Leu | Ser | Val | Glu |
| | | | 180 | | | | | 185 | | | | | 190 | | |
| Trp | Leu | Asn | Phe | Asp | Pro | Ser | Pro | Asp | Asp | Ser | Thr | Gly | Asn | Tyr | Ile |
| | | 195 | | | | | 200 | | | | | 205 | | | |
| Ala | Val | Gly | Asn | Met | Thr | Pro | Val | Ile | Glu | Val | Trp | Asp | Leu | Asp | Ile |
| | | 210 | | | | | 215 | | | | | 220 | | | |
| Val | Asp | Ser | Leu | Glu | Pro | Val | Phe | Thr | Leu | Gly | Ser | Lys | Leu | Ser | Lys |
| 225 | | | | | 230 | | | | | 235 | | | | | 240 |
| Lys | Lys | Lys | Lys | Lys | Gly | Lys | Lys | Ser | Ser | Ser | Ala | Glu | Gly | His | Thr |
| | | | | 245 | | | | | 250 | | | | | 255 | |
| Asp | Ala | Val | Leu | Asp | Leu | Ser | Trp | Asn | Lys | Leu | Ile | Arg | Asn | Val | Leu |
| | | | | 260 | | | | | 265 | | | | | 270 | |
| Ala | Ser | Ala | Ser | Ala | Asp | Asn | Thr | Val | Ile | Leu | Trp | Asp | Met | Ser | Leu |
| | | | 275 | | | | | 280 | | | | | 285 | | |
| Gly | Lys | Pro | Ala | Ala | Ser | Leu | Ala | Val | His | Thr | Asp | Lys | Val | Gln | Thr |
| | | 290 | | | | | 295 | | | | | 300 | | | |
| Leu | Gln | Phe | His | Pro | Phe | Glu | Ala | Gln | Thr | Leu | Ile | Ser | Gly | Ser | Tyr |
| 305 | | | | | 310 | | | | | 315 | | | | | 320 |
| Asp | Lys | Ser | Val | Ala | Leu | Tyr | Asp | Cys | Arg | Ser | Pro | Asp | Glu | Ser | His |
| | | | | 325 | | | | | 330 | | | | | 335 | |
| Arg | Met | Trp | Arg | Phe | Ser | Gly | Gln | Ile | Glu | Arg | Val | Thr | Trp | Asn | His |
| | | | 340 | | | | | 345 | | | | | 350 | | |
| Phe | Ser | Pro | Cys | His | Phe | Leu | Ala | Ser | Thr | Asp | Asp | Gly | Phe | Val | Tyr |
| | | 355 | | | | | 360 | | | | | 365 | | | |
| Asn | Leu | Asp | Ala | Arg | Ser | Asp | Lys | Pro | Ile | Phe | Thr | Leu | Asn | Ala | His |
| | | 370 | | | | | 375 | | | | | 380 | | | |
| Asn | Asp | Glu | Ile | Ser | Gly | Leu | Asp | Leu | Ser | Ser | Gln | Ile | Lys | Gly | Cys |

```
            385                          390                          395                         400
        Leu  Val  Thr  Ala  Ser  Ala  Asp  Lys  Tyr  Val  Lys  Ile  Trp  Asp  Ile  Leu
                            405                      410                      415

Gly  Asp  Arg  Pro  Ser  Leu  Val  His  Ser  Arg  Asp  Met  Lys  Met  Gly  Val
                            420                      425                      430

Leu  Phe  Cys  Ser  Ser  Cys  Cys  Pro  Asp  Leu  Pro  Phe  Ile  Tyr  Ala  Phe
                       435                      440                      445

Gly  Gly  Gln  Lys  Glu  Gly  Leu  Arg  Val  Trp  Asp  Ile  Ser  Thr  Val  Ser
                  450                      455                      460

Ser  Val  Asn  Glu  Ala  Phe  Gly  Arg  Arg  Glu  Arg  Leu  Val  Leu  Gly  Ser
        465                      470                      475                      480

Ala  Arg  Asn  Ser  Ser  Ile  Ser  Gly  Pro  Phe  Gly  Ser  Arg  Ser  Ser  Asp
                            485                      490                      495

Thr  Pro  Met  Glu  Ser
                       500
```

( 2 ) INFORMATION FOR SEQ ID NO:11:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:11:

```
        Asp  Tyr  Ser  Gln  Tyr  Tyr  Arg
        1                   5
```

( 2 ) INFORMATION FOR SEQ ID NO:12:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:12:

```
        Asn  His  Glu  Glu  Glu  Met  Asn  Ala  Leu  Arg
        1                   5                        10
```

( 2 ) INFORMATION FOR SEQ ID NO:13:

( i ) SEQUENCE CHARACTERISTICS:
        ( A ) LENGTH: 13 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:13:

```
        Leu  Leu  Glu  Gly  Glu  Asp  Ala  His  Leu  Thr  Gln  Tyr  Lys
        1                   5                        10
```

( 2 ) INFORMATION FOR SEQ ID NO:14:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:14:

Ile Leu Asn Glu Met Arg
 1               5

( 2 ) INFORMATION FOR SEQ ID NO:15:

( i ) SEQUENCE CHARACTERISTICS:
      ( A ) LENGTH: 7 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO:15:

Ser Glu Ile Ser Glu Leu Arg
 1               5

( 2 ) INFORMATION FOR SEQ ID NO:16:

( i ) SEQUENCE CHARACTERISTICS:
      ( A ) LENGTH: 9 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO:16:

Asp Ala Glu Asp Trp Phe Phe Ser Lys
 1               5

( 2 ) INFORMATION FOR SEQ ID NO:17:

( i ) SEQUENCE CHARACTERISTICS:
      ( A ) LENGTH: 11 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO:17:

Leu Ser Val Glu Ala Asp Ile Asn Gly Leu Arg
 1               5                   1 0

( 2 ) INFORMATION FOR SEQ ID NO:18:

( i ) SEQUENCE CHARACTERISTICS:
      ( A ) LENGTH: 432 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO:18:

Met Thr Thr Ser Ile Arg Gln Phe Thr Ser Ser Ser Ser Ile Lys Gly
 1               5                   1 0                  1 5

Ser Ser Gly Leu Gly Gly Gly Ser Ser Arg Thr Ser Cys Arg Leu Ser
                 2 0                  2 5                  3 0

Gly Gly Leu Gly Ala Gly Ser Cys Arg Leu Gly Ser Ala Gly Gly Leu
                 3 5                  4 0                  4 5

Gly Ser Thr Leu Gly Gly Ser Ser Tyr Ser Ser Cys Tyr Ser Phe Gly
         5 0                    5 5                  6 0

-continued

| | | | | | | | | | | | | | |
|---|---|---|---|---|---|---|---|---|---|---|---|---|---|
| Ser 65 | Gly | Gly | Gly | Tyr | Gly 70 | Ser | Ser | Phe | Gly | Gly 75 | Val | Asp | Gly | Leu | Leu 80 |
| Ala | Gly | Gly | Glu | Lys 85 | Ala | Thr | Met | Gln | Asn 90 | Leu | Asn | Asp | Arg | Leu 95 | Ala |
| Ser | Tyr | Leu | Asp 100 | Lys | Val | Arg | Ala | Leu 105 | Glu | Glu | Ala | Asn | Thr 110 | Glu | Leu |
| Glu | Val | Lys 115 | Ile | Arg | Asp | Trp | Tyr 120 | Gln | Arg | Gln | Ala | Pro 125 | Gly | Pro | Ala |
| Arg | Asp 130 | Tyr | Ser | Gln | Tyr | Tyr 135 | Arg | Thr | Ile | Glu | Glu 140 | Leu | Gln | Asn | Lys |
| Ile 145 | Leu | Thr | Ala | Thr | Val 150 | Asp | Asn | Ala | Asn | Ile 155 | Leu | Leu | Gln | Ile | Asp 160 |
| Asn | Ala | Arg | Leu | Ala 165 | Ala | Asp | Asp | Phe | Arg 170 | Thr | Lys | Phe | Glu | Thr 175 | Glu |
| Gln | Ala | Leu | Arg 180 | Leu | Ser | Val | Glu | Ala 185 | Asp | Ile | Asn | Gly | Leu 190 | Arg | Arg |
| Val | Leu | Asp 195 | Glu | Leu | Thr | Leu | Ala 200 | Arg | Ala | Asp | Leu | Glu 205 | Met | Gln | Ile |
| Glu | Asn 210 | Leu | Lys | Glu | Glu | Leu 215 | Ala | Tyr | Leu | Lys | Lys 220 | Asn | His | Glu | Glu |
| Glu 225 | Met | Asn | Ala | Leu | Arg 230 | Gly | Gln | Val | Gly | Gly 235 | Glu | Ile | Asn | Val | Glu 240 |
| Met | Asp | Ala | Ala | Pro 245 | Gly | Val | Asp | Leu | Ser 250 | Arg | Ile | Leu | Asn | Glu 255 | Met |
| Arg | Asp | Gln | Tyr 260 | Glu | Lys | Met | Ala | Glu 265 | Lys | Asn | Arg | Lys | Asp 270 | Ala | Glu |
| Asp | Trp | Phe 275 | Phe | Ser | Lys | Thr | Glu 280 | Glu | Leu | Asn | Arg | Glu 285 | Val | Ala | Thr |
| Asn | Ser 290 | Glu | Leu | Val | Gln | Ser 295 | Gly | Lys | Ser | Glu | Ile 300 | Ser | Glu | Leu | Arg |
| Arg 305 | Thr | Met | Gln | Ala | Leu 310 | Glu | Ile | Glu | Leu | Gln 315 | Ser | Gln | Leu | Ser | Met 320 |
| Lys | Ala | Ser | Leu | Glu 325 | Gly | Asn | Leu | Ala | Glu 330 | Thr | Glu | Asn | Arg | Tyr 335 | Cys |
| Val | Gln | Leu | Ser 340 | Gln | Ile | Gln | Gly | Leu 345 | Ile | Gly | Ser | Val | Glu 350 | Glu | Gln |
| Leu | Ala | Gln 355 | Leu | Arg | Cys | Glu | Met 360 | Glu | Gln | Gln | Asn | Gln 365 | Glu | Tyr | Lys |
| Ile | Leu | Leu 370 | Asp | Val | Lys | Thr | Arg 375 | Leu | Glu | Gln | Glu | Ile 380 | Ala | Thr | Tyr |
| Arg 385 | Arg | Leu | Leu | Glu | Gly 390 | Glu | Asp | Ala | His | Leu 395 | Thr | Gln | Tyr | Lys | Lys 400 |
| Glu | Pro | Val | Thr | Thr 405 | Arg | Gln | Val | Arg | Thr 410 | Ile | Val | Glu | Glu | Val 415 | Gln |
| Asp | Gly | Lys | Val 420 | Ile | Ser | Ser | Arg | Glu 425 | Gln | Val | His | Gln | Thr 430 | Thr | Arg |

(2) INFORMATION FOR SEQ ID NO:19:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide ( x i ) SEQUENCE DESCRIPTION: SEQ ID NO:19:

Phe Gly Gly Asn Pro Gly Gly Phe Gly Asn Gln Gly Gly Phe Gly Asn
1               5                   10                  15

Ser Arg ( 2 ) INFORMATION FOR SEQ ID NO:20:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:20:

Trp Cys Asp Cys Lys
1               5

( 2 ) INFORMATION FOR SEQ ID NO:21:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:21:

Thr Thr Glu Gln Asp Leu Lys
1               5

( 2 ) INFORMATION FOR SEQ ID NO:22:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:22:

Gly Phe Gly Phe Val Arg
1               5

( 2 ) INFORMATION FOR SEQ ID NO:23:

( i ) SEQUENCE CHARACTERISTICS:
        ( A ) LENGTH: 13 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:23:

Leu Pro Asn Ser Lys Gln Ser Gln Asp Glu Pro Leu Arg
1               5                   10

( 2 ) INFORMATION FOR SEQ ID NO:24:

( i ) SEQUENCE CHARACTERISTICS:
        ( A ) LENGTH: 12 amino acids
        ( B ) TYPE: amino acid
        ( C ) STRANDEDNESS:
        ( D ) TOPOLOGY: linear (i) MOLECULE TYPE: peptide (xi) SEQUENCE DESCRIPTION: SEQ ID NO:24:

| Lys | Met | Asp | Glu | Thr | Asp | Ala | Ser | Ser | Ala | Val | Lys |
|-----|-----|-----|-----|-----|-----|-----|-----|-----|-----|-----|-----|
| 1   |     |     |     | 5   |     |     |     |     | 10  |     |     |

(2) INFORMATION FOR SEQ ID NO:25:

(i) SEQUENCE CHARACTERISTICS:
(A) LENGTH: 12 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:25:

| Thr | Ser | Asp | Leu | Ile | Val | Leu | Gly | Leu | Pro | Trp | Lys |
|-----|-----|-----|-----|-----|-----|-----|-----|-----|-----|-----|-----|
| 1   |     |     |     | 5   |     |     |     |     | 10  |     |     |

(2) INFORMATION FOR SEQ ID NO:26:

(i) SEQUENCE CHARACTERISTICS:
(A) LENGTH: 414 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:26:

| Met | Ser | Glu | Tyr | Ile | Arg | Val | Thr | Glu | Asp | Glu | Asn | Asp | Glu | Pro | Ile |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Glu | Ile | Pro | Ser | Glu | Asp | Gly | Thr | Val | Leu | Leu | Ser | Thr | Val | Thr |     |
|     |     |     | 20  |     |     |     |     | 25  |     |     |     |     | 30  |     |     |
| Ala | Gln | Phe | Pro | Gly | Ala | Cys | Gly | Leu | Arg | Tyr | Arg | Asn | Pro | Val | Ser |
|     |     | 35  |     |     |     |     | 40  |     |     |     |     | 45  |     |     |     |
| Gln | Cys | Met | Arg | Gly | Val | Arg | Leu | Val | Glu | Gly | Ile | Leu | His | Ala | Pro |
|     | 50  |     |     |     |     | 55  |     |     |     |     | 60  |     |     |     |     |
| Asp | Ala | Gly | Trp | Gly | Asn | Leu | Val | Tyr | Val | Val | Asn | Tyr | Pro | Lys | Asp |
| 65  |     |     |     |     | 70  |     |     |     |     | 75  |     |     |     |     | 80  |
| Asn | Lys | Arg | Lys | Met | Asp | Glu | Thr | Asp | Ala | Ser | Ser | Ala | Val | Lys | Val |
|     |     |     |     | 85  |     |     |     |     | 90  |     |     |     |     | 95  |     |
| Lys | Arg | Ala | Val | Gln | Lys | Thr | Ser | Asp | Leu | Ile | Val | Leu | Gly | Leu | Pro |
|     |     |     | 100 |     |     |     |     | 105 |     |     |     |     | 110 |     |     |
| Trp | Lys | Thr | Thr | Glu | Gln | Asp | Leu | Lys | Glu | Tyr | Phe | Ser | Thr | Phe | Gly |
|     |     | 115 |     |     |     |     | 120 |     |     |     |     | 125 |     |     |     |
| Glu | Val | Leu | Met | Val | Gln | Val | Lys | Lys | Asp | Leu | Lys | Thr | Gly | His | Ser |
|     | 130 |     |     |     |     | 135 |     |     |     |     | 140 |     |     |     |     |
| Lys | Gly | Phe | Gly | Phe | Val | Arg | Phe | Thr | Glu | Tyr | Glu | Thr | Gln | Val | Lys |
| 145 |     |     |     |     | 150 |     |     |     |     | 155 |     |     |     |     | 160 |
| Val | Met | Ser | Gln | Arg | His | Met | Ile | Asp | Gly | Arg | Trp | Cys | Asp | Cys | Lys |
|     |     |     |     | 165 |     |     |     |     | 170 |     |     |     |     | 175 |     |
| Leu | Pro | Asn | Ser | Lys | Gln | Ser | Gln | Asp | Glu | Pro | Leu | Arg | Ser | Arg | Lys |
|     |     |     | 180 |     |     |     |     | 185 |     |     |     |     | 190 |     |     |
| Val | Phe | Val | Gly | Arg | Cys | Thr | Glu | Asp | Met | Thr | Glu | Asp | Glu | Leu | Arg |
|     |     | 195 |     |     |     |     | 200 |     |     |     |     | 205 |     |     |     |
| Glu | Phe | Phe | Ser | Gln | Tyr | Gly | Asp | Val | Met | Asp | Val | Phe | Ile | Pro | Lys |
|     | 210 |     |     |     |     | 215 |     |     |     |     | 220 |     |     |     |     |
| Pro | Phe | Arg | Ala | Phe | Ala | Phe | Val | Thr | Phe | Ala | Asp | Asp | Gln | Ile | Ala |
| 225 |     |     |     |     | 230 |     |     |     |     | 235 |     |     |     |     | 240 |

```
      Gln  Ser  Leu  Cys  Gly  Glu  Asp  Leu  Ile  Ile  Lys  Gly  Ile  Ser  Val  His
                      245                      250                     255

Ile  Ser  Asn  Ala  Glu  Pro  Lys  His  Asn  Ser  Asn  Arg  Gln  Leu  Glu  Arg
                      260                      265                     270

Ser  Gly  Arg  Phe  Gly  Gly  Asn  Pro  Gly  Gly  Phe  Gly  Asn  Gln  Gly  Gly
                 275                      280                     285

Phe  Gly  Asn  Ser  Arg  Gly  Gly  Gly  Ala  Gly  Leu  Gly  Asn  Asn  Gln  Gly
           290                           295                     300

Ser  Asn  Met  Gly  Gly  Gly  Met  Asn  Phe  Gly  Ala  Phe  Ser  Ile  Asn  Pro
      305                      310                     315                          320

Ala  Met  Met  Ala  Ala  Ala  Gln  Ala  Ala  Leu  Gln  Ser  Ser  Trp  Gly  Met
                           325                      330                     335

Met  Gly  Met  Leu  Ala  Ser  Gln  Gln  Asn  Gln  Ser  Gly  Pro  Ser  Gly  Asn
                      340                      345                     350

Asn  Gln  Asn  Gln  Gly  Asn  Met  Gln  Arg  Glu  Pro  Asn  Gln  Ala  Phe  Gly
                 355                      360                     365

Ser  Gly  Asn  Asn  Ser  Tyr  Ser  Gly  Ser  Asn  Ser  Gly  Ala  Ala  Ile  Gly
           370                      375                     380

Trp  Gly  Ser  Ala  Ser  Asn  Ala  Gly  Ser  Gly  Ser  Gly  Phe  Asn  Gly  Gly
      385                      390                     395                          400

Phe  Gly  Ser  Ser  Met  Asp  Ser  Lys  Ser  Ser  Gly  Trp  Gly  Met
                      405                      410
```

( 2 ) INFORMATION FOR SEQ ID NO:27:

( i ) SEQUENCE CHARACTERISTICS:
    ( A ) LENGTH: 4 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:27:

Asn  Tyr  Tyr  Arg
   1

( 2 ) INFORMATION FOR SEQ ID NO:28:

( i ) SEQUENCE CHARACTERISTICS:
    ( A ) LENGTH: 4 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:28:

Asn  Tyr  Tyr  Arg
   1

( 2 ) INFORMATION FOR SEQ ID NO:29:

( i ) SEQUENCE CHARACTERISTICS:
    ( A ) LENGTH: 6 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:29:

Val  Gln  Glu  Ala  Gln  Lys (2) INFORMATION FOR SEQ ID NO:30:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:30:

```
Glu  Val  Ala  Asp  Cys  Phe  Lys
 1                 5
```

(2) INFORMATION FOR SEQ ID NO:31:

(i) SEQUENCE CHARACTERISTICS:
        (A) LENGTH: 22 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:31:

```
His  Asp  Gly  Thr  Gly  Gly  Gln  Ser  Ile  Tyr  Gly  Asp  Lys  Phe  Glu  Asp
 1                 5                           10                          15
Glu  Asn  Phe  Asp  Val  Lys
                20
```

(2) INFORMATION FOR SEQ ID NO:32:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:32:

```
Ile  Thr  Met  Glu  Leu  Phe  Xaa  Asn  Ile  Val  Pro  Arg
 1                 5                           10
```

(2) INFORMATION FOR SEQ ID NO:33:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:33:

```
His  Thr  Gly  Pro  Gly  Leu  Leu  Ser  Met  Ala  Asn  Gln  Gly  Gln  Asn  Thr
 1                 5                           10                          15
Asn  Asn  Xaa  Xaa  Phe  Val  Ile  Xaa  Leu  Lys
                20                      25
```

(2) INFORMATION FOR SEQ ID NO:34:

(i) SEQUENCE CHARACTERISTICS:
        (A) LENGTH: 3224 amino acids
        (B) TYPE: amino acid
        (C) STRANDEDNESS:
        (D) TOPOLOGY: linear ( i i ) MOLECULE TYPE: peptide ( x i ) SEQUENCE DESCRIPTION: SEQ ID NO:34:

| Met | Arg | Arg | Ser | Lys | Ala | Asp | Val | Glu | Arg | Tyr | Ile | Ala | Ser | Val | Gln |
|---|---|---|---|---|---|---|---|---|---|---|---|---|---|---|---|
| 1 | | | | 5 | | | | | 10 | | | | | 15 | |
| Gly | Ser | Thr | Pro | Ser | Pro | Arg | Gln | Lys | Ser | Met | Lys | Gly | Phe | Tyr | Phe |
| | | | 20 | | | | 25 | | | | | 30 | | | |
| Ala | Lys | Leu | Tyr | Tyr | Glu | Ala | Lys | Glu | Tyr | Asp | Leu | Ala | Lys | Lys | Tyr |
| | | 35 | | | | 40 | | | | | 45 | | | | |
| Ile | Cys | Thr | Tyr | Ile | Asn | Val | Gln | Glu | Arg | Asp | Pro | Lys | Ala | His | Arg |
| | 50 | | | | | 55 | | | | | 60 | | | | |
| Phe | Leu | Gly | Leu | Leu | Tyr | Glu | Leu | Glu | Glu | Asn | Thr | Asp | Lys | Ala | Val |
| 65 | | | | | 70 | | | | | 75 | | | | | 80 |
| Glu | Cys | Tyr | Arg | Arg | Ser | Val | Glu | Leu | Asn | Pro | Thr | Gln | Lys | Asp | Leu |
| | | | | 85 | | | | | 90 | | | | | 95 | |
| Val | Leu | Lys | Ile | Ala | Glu | Leu | Leu | Cys | Lys | Asn | Asp | Val | Thr | Asp | Gly |
| | | | 100 | | | | | 105 | | | | | 110 | | |
| Arg | Ala | Lys | Tyr | Trp | Leu | Glu | Arg | Ala | Ala | Lys | Leu | Phe | Pro | Gly | Ser |
| | | 115 | | | | | 120 | | | | | 125 | | | |
| Pro | Ala | Ile | Tyr | Lys | Leu | Lys | Glu | Gln | Leu | Leu | Asp | Cys | Glu | Gly | Glu |
| 130 | | | | | 135 | | | | | 140 | | | | | |
| Asp | Gly | Trp | Asn | Lys | Leu | Phe | Asp | Leu | Ile | Gln | Ser | Glu | Leu | Tyr | Val |
| 145 | | | | | 150 | | | | | 155 | | | | | 160 |
| Arg | Pro | Asp | Asp | Val | His | Val | Asn | Ile | Arg | Leu | Val | Glu | Val | Tyr | Arg |
| | | | | 165 | | | | | 170 | | | | | 175 | |
| Ser | Thr | Lys | Arg | Leu | Lys | Asp | Ala | Val | Ala | His | Cys | His | Glu | Ala | Glu |
| | | | 180 | | | | | 185 | | | | | 190 | | |
| Arg | Asn | Ile | Ala | Leu | Arg | Ser | Ser | Leu | Glu | Trp | Asn | Ser | Cys | Val | Val |
| | | 195 | | | | | 200 | | | | | 205 | | | |
| Gln | Thr | Leu | Lys | Glu | Tyr | Leu | Glu | Ser | Leu | Gln | Cys | Leu | Glu | Ser | Asp |
| | 210 | | | | | 215 | | | | | 220 | | | | |
| Lys | Ser | Asp | Trp | Arg | Ala | Thr | Asn | Thr | Asp | Leu | Leu | Leu | Ala | Tyr | Ala |
| 225 | | | | | 230 | | | | | 235 | | | | | 240 |
| Asn | Leu | Met | Leu | Leu | Thr | Leu | Ser | Thr | Arg | Asp | Val | Gln | Glu | Ser | Arg |
| | | | | 245 | | | | | 250 | | | | | 255 | |
| Glu | Leu | Leu | Gln | Ser | Phe | Asp | Ser | Ala | Leu | Gln | Ser | Val | Lys | Ser | Leu |
| | | | 260 | | | | | 265 | | | | | 270 | | |
| Gly | Gly | Asn | Asp | Glu | Leu | Ser | Ala | Thr | Phe | Leu | Glu | Met | Lys | Gly | His |
| | | 275 | | | | | 280 | | | | | 285 | | | |
| Phe | Tyr | Met | His | Ala | Gly | Ser | Leu | Leu | Leu | Lys | Met | Gly | Gln | His | Ser |
| 290 | | | | | 295 | | | | | 300 | | | | | |
| Ser | Asn | Val | Gln | Trp | Arg | Ala | Leu | Ser | Glu | Leu | Ala | Ala | Leu | Cys | Tyr |
| 305 | | | | | 310 | | | | | 315 | | | | | 320 |
| Leu | Ile | Ala | Phe | Gln | Val | Pro | Arg | Pro | Lys | Ile | Lys | Leu | Ile | Lys | Gly |
| | | | | 325 | | | | | 330 | | | | | 335 | |
| Glu | Ala | Gly | Gln | Asn | Leu | Leu | Glu | Met | Met | Ala | Cys | Asp | Arg | Leu | Ser |
| | | | 340 | | | | | 345 | | | | | 350 | | |
| Gln | Ser | Gly | His | Met | Leu | Leu | Asn | Leu | Ser | Arg | Gly | Lys | Gln | Asp | Phe |
| | | 355 | | | | | 360 | | | | | 365 | | | |
| Leu | Lys | Glu | Ile | Val | Glu | Thr | Phe | Ala | Asn | Lys | Ser | Gly | Gln | Ser | Ala |
| 370 | | | | | 375 | | | | | 380 | | | | | |
| Leu | Tyr | Asp | Ala | Leu | Phe | Ser | Ser | Gln | Ser | Pro | Lys | Asp | Thr | Ser | Phe |
| 385 | | | | | 390 | | | | | 395 | | | | | 400 |

```
Leu Gly Ser Asp Asp Ile Gly Asn Ile Asp Val Arg Glu Pro Glu Leu
                405                 410                 415
Glu Asp Leu Thr Arg Tyr Asp Val Gly Ala Ile Arg Ala His Asn Gly
                420                 425                 430
Ser Leu Gln His Leu Thr Trp Leu Gly Leu Gln Trp Asn Ser Leu Pro
                435                 440                 445
Ala Leu Pro Gly Ile Arg Lys Trp Leu Lys Gln Leu Phe His His Leu
                450                 455                 460
Pro His Glu Thr Ser Arg Leu Glu Thr Asn Ala Pro Glu Ser Ile Cys
465                 470                 475                 480
Ile Leu Asp Leu Glu Val Phe Leu Leu Gly Val Val Tyr Thr Ser His
                        485                 490                 495
Leu Gln Leu Lys Glu Lys Cys Asn Ser His His Ser Ser Tyr Gln Pro
                500                 505                 510
Leu Cys Leu Pro Leu Pro Val Cys Lys Gln Leu Cys Thr Glu Arg Gln
                515                 520                 525
Lys Ser Trp Trp Asp Ala Val Cys Thr Leu Ile His Arg Lys Ala Val
                530                 535                 540
Pro Gly Asn Val Ala Lys Leu Arg Leu Leu Val Gln His Glu Ile Asn
545                 550                 555                 560
Thr Leu Arg Ala Gln Glu Lys His Gly Leu Gln Pro Ala Leu Leu Val
                        565                 570                 575
His Trp Ala Glu Cys Leu Gln Lys Thr Gly Ser Gly Leu Asn Ser Phe
                580                 585                 590
Tyr Asp Gln Arg Glu Tyr Ile Gly Arg Ser Val His Tyr Trp Lys Lys
                595                 600                 605
Val Leu Pro Leu Leu Lys Ile Ile Lys Lys Asn Ser Ile Pro Glu
    610                 615                 620
Pro Ile Asp Pro Leu Phe Lys His Phe His Ser Val Asp Ile Gln Ala
625                 630                 635                 640
Ser Glu Ile Val Glu Tyr Glu Glu Asp Ala His Ile Thr Phe Ala Ile
                    645                 650                 655
Leu Asp Ala Val Asn Gly Asn Ile Glu Asp Ala Val Thr Ala Phe Glu
                660                 665                 670
Ser Ile Lys Ser Val Val Ser Tyr Trp Asn Leu Ala Leu Ile Phe His
        675                 680                 685
Arg Lys Ala Glu Asp Ile Glu Asn Asp Ala Leu Ser Pro Glu Glu Gln
        690                 695                 700
Glu Glu Cys Lys Asn Tyr Leu Arg Lys Thr Arg Asp Tyr Leu Ile Lys
705                 710                 715                 720
Ile Ile Asp Asp Ser Asp Ser Asn Leu Ser Val Val Lys Lys Leu Pro
                725                 730                 735
Val Pro Leu Glu Ser Val Lys Glu Met Leu Asn Ser Val Met Gln Glu
                740                 745                 750
Leu Glu Asp Tyr Ser Glu Gly Gly Pro Leu Tyr Lys Asn Gly Ser Leu
            755                 760                 765
Arg Asn Ala Asp Ser Glu Ile Lys Arg Ser Thr Pro Ser Pro Thr Arg
            770                 775                 780
Tyr Ser Leu Ser Pro Ser Lys Ser Tyr Lys Tyr Ser Pro Lys Thr Pro
785                 790                 795                 800
Pro Arg Trp Ala Glu Asp Gln Asn Ser Leu Leu Lys Met Ile Cys Gln
                805                 810                 815
Gln Val Glu Ala Ile Lys Lys Glu Met Gln Glu Leu Lys Leu Asn Ser
                820                 825                 830
```

```
Ser Asn Ser Ala Ser Pro His Arg Trp Pro Thr Glu Asn Tyr Gly Pro
            835                 840                 845

Asp Ser Val Pro Asp Gly Tyr Gln Gly Ser Gln Thr Phe His Gly Ala
850                 855                 860

Pro Leu Thr Val Ala Thr Thr Gly Pro Ser Val Tyr Tyr Ser Gln Ser
865                 870                 875                 880

Pro Ala Tyr Asn Ser Gln Tyr Leu Leu Arg Pro Ala Ala Asn Val Thr
            885                 890                 895

Pro Thr Lys Gly Pro Val Tyr Gly Met Asn Arg Leu Pro Pro Gln Gln
            900                 905                 910

His Ile Tyr Ala Tyr Pro Gln Gln Met His Thr Pro Pro Val Gln Ser
            915                 920                 925

Ser Ser Ala Cys Met Phe Ser Gln Glu Met Tyr Gly Pro Pro Ala Leu
930                 935                 940

Arg Phe Glu Ser Pro Ala Thr Gly Ile Leu Ser Pro Arg Gly Asp Asp
945                 950                 955                 960

Tyr Phe Asn Tyr Asn Val Gln Gln Thr Ser Thr Asn Pro Pro Leu Pro
            965                 970                 975

Glu Pro Gly Tyr Phe Thr Lys Pro Pro Ile Ala Ala His Ala Ser Arg
            980                 985                 990

Ser Ala Glu Ser Lys Thr Ile Glu Phe Gly Lys Thr Asn Phe Val Gln
            995                 1000                1005

Pro Met Pro Gly Glu Gly Leu Arg Pro Ser Leu Pro Thr Gln Ala His
            1010                1015                1020

Thr Thr Gln Pro Thr Pro Phe Lys Phe Asn Ser Asn Phe Lys Ser Asn
1025                1030                1035                1040

Asp Gly Asp Phe Thr Phe Ser Ser Pro Gln Val Val Thr Gln Pro Pro
            1045                1050                1055

Pro Ala Ala Tyr Ser Asn Ser Glu Ser Leu Leu Gly Leu Leu Thr Ser
            1060                1065                1070

Asp Lys Pro Leu Gln Gly Asp Gly Tyr Ser Gly Ala Lys Pro Ile Pro
            1075                1080                1085

Gly Gly Gln Thr Ile Gly Pro Arg Asn Thr Phe Asn Phe Gly Ser Lys
            1090                1095                1100

Asn Val Ser Gly Ile Ser Phe Thr Glu Asn Met Gly Ser Ser Gln Gln
1105                1110                1115                1120

Lys Asn Ser Gly Phe Arg Arg Ser Asp Asp Met Phe Thr Phe His Gly
            1125                1130                1135

Pro Gly Lys Ser Val Phe Gly Thr Pro Thr Leu Glu Thr Ala Asn Lys
            1140                1145                1150

Asn His Glu Thr Asp Gly Gly Ser Ala His Gly Asp Asp Asp Asp Asp
            1155                1160                1165

Gly Pro His Phe Glu Pro Val Val Pro Leu Pro Asp Lys Ile Glu Val
            1170                1175                1180

Lys Thr Gly Glu Glu Asp Glu Glu Glu Phe Phe Cys Asn Arg Ala Lys
1185                1190                1195                1200

Leu Phe Arg Phe Asp Val Glu Ser Lys Glu Trp Lys Glu Arg Gly Ile
            1205                1210                1215

Gly Asn Val Lys Ile Leu Arg His Lys Thr Ser Gly Lys Ile Arg Leu
            1220                1225                1230

Leu Met Arg Arg Glu Gln Val Leu Lys Ile Cys Ala Asn His Tyr Ile
            1235                1240                1245

Ser Pro Asp Met Lys Leu Thr Pro Asn Ala Gly Ser Asp Arg Ser Phe
```

```
                    1250                    1255                    1260
Val  Trp  His  Ala  Leu  Asp  Tyr  Ala  Asp  Glu  Leu  Pro  Lys  Pro  Glu  Gln
1265                     1270                    1275                    1280
Leu  Ala  Ile  Arg  Phe  Lys  Thr  Pro  Glu  Glu  Ala  Ala  Leu  Phe  Lys  Cys
                    1285                    1290                    1295
Lys  Phe  Glu  Glu  Ala  Gln  Ser  Ile  Leu  Lys  Ala  Pro  Gly  Thr  Asn  Val
                    1300                    1305                    1310
Ala  Met  Ala  Ser  Asn  Gln  Ala  Val  Arg  Ile  Val  Lys  Glu  Pro  Thr  Ser
                    1315                    1320                    1325
His  Asp  Asn  Lys  Asp  Ile  Cys  Lys  Ser  Asp  Ala  Gly  Asn  Leu  Asn  Phe
                    1330                    1335                    1340
Glu  Phe  Gln  Val  Ala  Lys  Lys  Glu  Gly  Ser  Trp  Trp  His  Cys  Asn  Ser
1345                     1350                    1355                    1360
Cys  Ser  Leu  Lys  Asn  Ala  Ser  Thr  Ala  Lys  Lys  Cys  Val  Ser  Cys  Gln
                    1365                    1370                    1375
Asn  Leu  Asn  Pro  Ser  Asn  Lys  Glu  Leu  Val  Gly  Pro  Pro  Leu  Ala  Glu
                    1380                    1385                    1390
Thr  Val  Phe  Thr  Pro  Lys  Thr  Ser  Pro  Glu  Asn  Val  Gln  Asp  Arg  Phe
                    1395                    1400                    1405
Ala  Leu  Val  Thr  Pro  Lys  Lys  Glu  Gly  His  Trp  Asp  Cys  Ser  Ile  Cys
                    1410                    1415                    1420
Leu  Val  Arg  Asn  Glu  Pro  Thr  Val  Ser  Arg  Cys  Ile  Ala  Cys  Gln  Asn
1425                     1430                    1435                    1440
Thr  Lys  Ser  Ala  Asn  Lys  Ser  Gly  Ser  Ser  Phe  Val  His  Gln  Ala  Ser
                    1445                    1450                    1455
Phe  Lys  Phe  Gly  Gln  Gly  Asp  Leu  Pro  Lys  Pro  Ile  Asn  Ser  Asp  Phe
                    1460                    1465                    1470
Arg  Ser  Val  Phe  Ser  Thr  Lys  Glu  Gly  Gln  Trp  Asp  Cys  Ser  Ala  Cys
                    1475                    1480                    1485
Leu  Val  Gln  Asn  Glu  Gly  Ser  Ser  Thr  Lys  Cys  Ala  Ala  Cys  Gln  Asn
                    1490                    1495                    1500
Pro  Arg  Lys  Gln  Ser  Leu  Pro  Ala  Thr  Ser  Ile  Pro  Thr  Pro  Ala  Ser
1505                     1510                    1515                    1520
Phe  Lys  Phe  Gly  Thr  Ser  Glu  Thr  Ser  Lys  Thr  Leu  Lys  Ser  Gly  Phe
                    1525                    1530                    1535
Glu  Asp  Met  Phe  Ala  Lys  Lys  Glu  Gly  Gln  Trp  Asp  Cys  Ser  Ser  Cys
                    1540                    1545                    1550
Leu  Val  Arg  Asn  Glu  Ala  Asn  Ala  Thr  Arg  Cys  Val  Ala  Cys  Gln  Asn
                    1555                    1560                    1565
Pro  Asp  Lys  Pro  Ser  Pro  Ser  Thr  Ser  Val  Pro  Ala  Pro  Ala  Ser  Phe
                    1570                    1575                    1580
Lys  Phe  Gly  Thr  Ser  Glu  Thr  Ser  Lys  Ala  Pro  Lys  Ser  Gly  Phe  Glu
1585                     1590                    1595                    1600
Gly  Met  Phe  Thr  Lys  Lys  Glu  Gly  Gln  Trp  Asp  Cys  Ser  Val  Cys  Leu
                    1605                    1610                    1615
Val  Arg  Asn  Glu  Ala  Ser  Ala  Thr  Lys  Cys  Ile  Ala  Cys  Gln  Asn  Pro
                    1620                    1625                    1630
Gly  Lys  Gln  Asn  Gln  Thr  Thr  Ser  Ala  Val  Ser  Thr  Pro  Ala  Ser  Ser
                    1635                    1640                    1645
Glu  Thr  Ser  Lys  Ala  Pro  Lys  Ser  Gly  Phe  Glu  Gly  Met  Phe  Thr  Lys
                    1650                    1655                    1660
Lys  Glu  Gly  Gln  Trp  Asp  Cys  Ser  Val  Cys  Leu  Val  Arg  Asn  Glu  Ala
1665                     1670                    1675                    1680
```

Ser Ala Thr Lys Cys Ile Ala Cys Gln Asn Pro Gly Lys Gln Asn Gln
            1685                1690                1695

Thr Thr Ser Ala Val Ser Thr Pro Ala Ser Ser Glu Thr Ser Lys Ala
       1700                1705                1710

Pro Lys Ser Gly Phe Glu Gly Met Phe Thr Lys Lys Gly Gln Trp
       1715                1720                1725

Asp Cys Ser Val Cys Leu Val Arg Asn Glu Ala Ser Ala Thr Lys Cys
       1730                1735                1740

Ile Ala Cys Gln Cys Pro Ser Lys Gln Asn Gln Thr Thr Ala Ile Ser
1745               1750                1755                1760

Thr Pro Ala Ser Ser Glu Ile Ser Lys Ala Pro Lys Ser Gly Phe Glu
            1765                1770                1775

Gly Met Phe Ile Arg Lys Gly Gln Trp Asp Cys Ser Val Cys Cys Val
       1780                1785                1790

Gln Asn Glu Ser Ser Ser Leu Lys Cys Val Ala Cys Asp Ala Ser Lys
       1795                1800                1805

Pro Thr His Lys Pro Ile Ala Glu Ala Pro Ser Ala Phe Thr Leu Gly
       1810                1815                1820

Ser Glu Met Lys Leu His Asp Ser Ser Gly Ser Gln Val Gly Thr Gly
1825               1830                1835                1840

Phe Lys Ser Asn Phe Ser Glu Lys Ala Ser Lys Phe Gly Asn Thr Glu
            1845                1850                1855

Gln Gly Phe Lys Phe Gly His Val Asp Gln Glu Asn Ser Pro Ser Phe
            1860                1865                1870

Met Phe Gln Gly Ser Ser Asn Thr Glu Phe Lys Ser Thr Lys Glu Gly
            1875                1880                1885

Phe Ser Ile Pro Val Ser Ala Asp Gly Phe Lys Phe Gly Ile Ser Glu
       1890                1895                1900

Pro Gly Asn Gln Glu Lys Lys Ser Glu Lys Pro Leu Glu Asn Gly Thr
1905               1910                1915                1920

Gly Phe Gln Ala Gln Asp Ile Ser Gly Gln Lys Asn Gly Arg Gly Val
                 1925                1930                1935

Ile Phe Gly Gln Thr Ser Ser Thr Phe Thr Phe Ala Asp Leu Ala Lys
            1940                1945                1950

Ser Thr Ser Gly Glu Gly Phe Gln Phe Gly Lys Lys Asp Pro Asn Phe
       1955                1960                1965

Lys Gly Phe Ser Gly Ala Gly Glu Lys Leu Phe Ser Ser Gln Tyr Gly
       1970                1975                1980

Lys Met Ala Asn Lys Ala Asn Thr Ser Gly Asp Phe Glu Lys Asp Asp
1985               1990                1995                2000

Asp Ala Tyr Lys Thr Glu Asp Ser Asp Asp Ile His Phe Glu Pro Val
            2005                2010                2015

Val Gln Met Pro Glu Lys Val Glu Leu Val Thr Gly Glu Glu Asp Glu
            2020                2025                2030

Lys Val Leu Tyr Ser Gln Arg Val Lys Leu Phe Arg Phe Asp Ala Glu
            2035                2040                2045

Val Ser Gln Trp Lys Glu Arg Gly Leu Gly Asn Leu Lys Ile Leu Lys
            2050                2055                2060

Asn Glu Val Asn Gly Lys Leu Arg Met Leu Met Arg Arg Glu Gln Val
2065               2070                2075                2080

Leu Lys Val Cys Ala Asn His Trp Ile Thr Thr Thr Met Asn Leu Lys
                 2085                2090                2095

Pro Leu Ser Gly Ser Asp Arg Ala Trp Met Trp Leu Ala Ser Asp Phe
            2100                2105                2110

```
Ser Asp Gly Asp Ala Lys Leu Glu Gln Leu Ala Ala Lys Phe Lys Thr
        2115                2120                2125
Pro Glu Leu Ala Glu Glu Phe Lys Gln Lys Phe Glu Glu Cys Gln Arg
        2130                2135                2140
Leu Leu Leu Asp Ile Pro Leu Gln Thr Pro His Lys Leu Val Asp Thr
2145                2150                2155                2160
Gly Arg Ala Ala Lys Leu Ile Gln Arg Ala Glu Glu Met Lys Ser Gly
        2165                2170                2175
Leu Lys Asp Phe Lys Thr Phe Leu Thr Asn Asp Gln Thr Lys Val Thr
        2180                2185                2190
Glu Glu Glu Asn Lys Gly Ser Gly Thr Gly Ala Ala Gly Ala Ser Asp
        2195                2200                2205
Thr Thr Ile Lys Pro Asn Pro Glu Asn Thr Gly Pro Thr Leu Glu Trp
        2210                2215                2220
Asp Asn Tyr Asp Leu Arg Glu Asp Ala Leu Asp Asp Ser Val Ser Ser
2225                2230                2235                2240
Ser Ser Val His Ala Ser Pro Leu Ala Ser Ser Pro Val Arg Lys Asn
                2245                2250                2255
Leu Phe Arg Phe Gly Glu Ser Thr Thr Gly Phe Asn Phe Ser Phe Lys
        2260                2265                2270
Ser Ala Leu Ser Pro Ser Lys Ser Pro Ala Lys Leu Asn Gln Ser Gly
        2275                2280                2285
Thr Ser Val Gly Thr Asp Glu Glu Ser Asp Val Thr Gln Glu Glu Glu
        2290                2295                2300
Arg Asp Gly Gln Tyr Phe Glu Pro Val Val Pro Leu Pro Asp Leu Val
2305                2310                2315                2320
Glu Val Ser Ser Gly Glu Glu Asn Glu Gln Val Val Phe Ser His Arg
                2325                2330                2335
Ala Lys Leu Tyr Arg Tyr Asp Lys Asp Val Gly Gln Trp Lys Glu Arg
        2340                2345                2350
Gly Ile Gly Asp Ile Lys Ile Leu Gln Asn Tyr Asp Asn Lys Gln Val
        2355                2360                2365
Arg Ile Val Met Arg Arg Asp Gln Val Leu Lys Leu Cys Ala Asn His
2370                2375                2380
Arg Ile Thr Pro Asp Met Thr Leu Gln Asn Met Lys Gly Thr Glu Arg
2385                2390                2395                2400
Val Trp Leu Trp Thr Ala Cys Asp Phe Ala Asp Gly Glu Arg Lys Val
        2405                2410                2415
Glu His Leu Ala Val Arg Phe Lys Leu Gln Asp Val Ala Asp Ser Phe
        2420                2425                2430
Lys Lys Ile Phe Asp Glu Ala Lys Thr Ala Gln Glu Lys Asp Ser Leu
        2435                2440                2445
Ile Thr Pro His Val Ser Arg Ser Ser Thr Pro Arg Glu Ser Pro Cys
        2450                2455                2460
Gly Lys Ile Ala Val Ala Val Leu Glu Glu Thr Thr Arg Glu Arg Thr
2465                2470                2475                2480
Asp Val Ile Gln Gly Asp Asp Val Ala Asp Ala Thr Ser Glu Val Glu
                2485                2490                2495
Val Ser Ser Thr Ser Glu Thr Thr Pro Lys Ala Val Val Ser Pro Pro
        2500                2505                2510
Lys Phe Val Phe Gly Ser Glu Ser Val Lys Ser Ile Phe Ser Ser Glu
        2515                2520                2525
Lys Ser Lys Pro Phe Ala Phe Gly Asn Ser Ser Ala Thr Gly Ser Leu
```

```
                    2530                      2535                      2540
  Phe  Gly  Phe  Ser  Phe  Asn  Ala  Pro  Leu  Lys  Ser  Asn  Asn  Ser  Glu  Thr
  2545                      2550                      2555                      2560

Ser  Ser  Val  Ala  Gln  Ser  Gly  Ser  Glu  Ser  Lys  Val  Glu  Pro  Lys  Lys
                       2565                      2570                      2575

Cys  Glu  Leu  Ser  Lys  Asn  Ser  Asp  Ile  Glu  Gln  Ser  Ser  Asp  Ser  Lys
                            2580                      2585                      2590

Val  Lys  Asn  Leu  Phe  Ala  Ser  Phe  Pro  Thr  Glu  Glu  Ser  Ser  Ile  Asn
                       2595                      2600                      2605

Tyr  Thr  Phe  Lys  Thr  Pro  Glu  Lys  Ala  Lys  Glu  Lys  Lys  Lys  Pro  Glu
                       2610                      2615                      2620

Asp  Ser  Pro  Ser  Asp  Asp  Val  Leu  Ile  Val  Tyr  Glu  Leu  Thr  Pro
  2625                      2630                      2635                      2640

Thr  Ala  Glu  Gln  Lys  Ala  Leu  Ala  Thr  Lys  Leu  Lys  Leu  Pro  Pro  Thr
                       2645                      2650                      2655

Phe  Phe  Cys  Tyr  Lys  Asn  Arg  Pro  Asp  Tyr  Val  Ser  Glu  Glu  Glu
                            2660                      2665                      2670

Asp  Asp  Glu  Asp  Phe  Glu  Thr  Ala  Val  Lys  Lys  Leu  Asn  Gly  Lys  Leu
                       2675                      2680                      2685

Tyr  Leu  Asp  Gly  Ser  Glu  Lys  Cys  Arg  Pro  Leu  Glu  Glu  Asn  Thr  Ala
                       2690                      2695                      2700

Asp  Asn  Glu  Lys  Glu  Cys  Ile  Ile  Val  Trp  Glu  Lys  Lys  Pro  Thr  Val
  2705                      2710                      2715                      2720

Glu  Glu  Lys  Ala  Lys  Ala  Asp  Thr  Leu  Lys  Leu  Pro  Pro  Thr  Phe  Phe
                            2725                      2730                      2735

Cys  Gly  Val  Cys  Ser  Asp  Thr  Asp  Glu  Asp  Asn  Gly  Asn  Gly  Glu  Asp
                            2740                      2745                      2750

Phe  Gln  Ser  Glu  Leu  Gln  Lys  Val  Gln  Glu  Ala  Gln  Lys  Ser  Gln  Thr
                       2755                      2760                      2765

Glu  Glu  Ile  Thr  Ser  Thr  Thr  Asp  Ser  Val  Tyr  Thr  Gly  Gly  Thr  Glu
                       2770                      2775                      2780

Val  Met  Val  Pro  Ser  Phe  Cys  Lys  Ser  Glu  Glu  Pro  Asp  Ser  Ile  Thr
  2785                      2790                      2795                      2800

Lys  Ser  Ile  Ser  Ser  Pro  Ser  Val  Ser  Ser  Glu  Thr  Met  Asp  Lys  Pro
                            2805                      2810                      2815

Val  Asp  Leu  Ser  Thr  Arg  Lys  Glu  Ile  Asp  Thr  Asp  Ser  Thr  Ser  Gln
                       2820                      2825                      2830

Gly  Glu  Ser  Lys  Ile  Val  Ser  Phe  Gly  Phe  Gly  Ser  Ser  Thr  Gly  Leu
                       2835                      2840                      2845

Ser  Phe  Ala  Asp  Leu  Ala  Ser  Ser  Asn  Ser  Gly  Asp  Phe  Ala  Phe  Gly
                       2850                      2855                      2860

Ser  Lys  Asp  Lys  Asn  Phe  Gln  Trp  Ala  Asn  Thr  Gly  Ala  Ala  Val  Phe
  2865                      2870                      2875                      2880

Gly  Thr  Gln  Ser  Val  Gly  Thr  Gln  Ser  Ala  Gly  Lys  Val  Gly  Glu  Asp
                            2885                      2890                      2895

Glu  Asp  Gly  Ser  Asp  Glu  Glu  Val  Val  His  Asn  Glu  Asp  Ile  His  Phe
                            2900                      2905                      2910

Glu  Pro  Ile  Val  Ser  Leu  Pro  Glu  Val  Glu  Val  Lys  Ser  Gly  Glu  Glu
                       2915                      2920                      2925

Asp  Glu  Glu  Ile  Leu  Phe  Lys  Glu  Arg  Ala  Lys  Leu  Tyr  Arg  Trp  Asp
                       2930                      2935                      2940

Arg  Asp  Val  Ser  Gln  Trp  Lys  Glu  Arg  Gly  Val  Gly  Asp  Ile  Lys  Ile
  2945                      2950                      2955                      2960
```

-continued

```
Leu  Trp  His  Thr  Met  Lys  Asn  Tyr  Tyr  Arg  Ile  Leu  Met  Arg  Arg  Asp
               2965                2970                     2975

Gln  Val  Phe  Lys  Val  Cys  Ala  Asn  His  Val  Ile  Thr  Lys  Thr  Met  Glu
               2980                2985                     2990

Leu  Lys  Pro  Leu  Asn  Val  Ser  Asn  Asn  Ala  Leu  Val  Trp  Thr  Ala  Ser
               2995                3000                     3005

Asp  Tyr  Ala  Asp  Gly  Glu  Ala  Lys  Val  Glu  Gln  Leu  Ala  Val  Arg  Phe
               3010                3015                     3020

Lys  Thr  Lys  Glu  Val  Ala  Asp  Cys  Phe  Lys  Lys  Thr  Phe  Glu  Glu  Cys
3025                3030                3035                               3040

Gln  Gln  Asn  Leu  Met  Lys  Leu  Gln  Lys  Gly  His  Val  Ser  Leu  Ala  Ala
               3045                3050                                    3055

Glu  Leu  Ser  Lys  Glu  Thr  Asn  Pro  Val  Val  Phe  Phe  Asp  Val  Cys  Ala
               3060                3065                     3070

Asp  Gly  Glu  Pro  Leu  Gly  Arg  Ile  Thr  Met  Glu  Leu  Phe  Ser  Asn  Ile
               3075                3080                     3085

Val  Pro  Arg  Thr  Ala  Glu  Asn  Phe  Arg  Ala  Leu  Cys  Thr  Gly  Glu  Lys
               3090                3095                     3100

Gly  Phe  Gly  Phe  Lys  Asn  Ser  Ile  Phe  His  Arg  Val  Ile  Pro  Asp  Phe
3105                3110                3115                               3120

Val  Cys  Gln  Gly  Gly  Asp  Ile  Thr  Lys  His  Asp  Gly  Thr  Gly  Gly  Gln
               3125                3130                     3135

Ser  Ile  Tyr  Gly  Asp  Lys  Phe  Glu  Asp  Glu  Asn  Phe  Asp  Val  Lys  His
               3140                3145                     3150

Thr  Gly  Pro  Gly  Leu  Leu  Ser  Met  Ala  Asn  Gln  Gly  Gln  Asn  Thr  Asn
               3155                3160                     3165

Asn  Ser  Gln  Phe  Val  Ile  Thr  Leu  Lys  Lys  Ala  Glu  His  Leu  Asp  Phe
               3170                3175                     3180

Lys  His  Val  Val  Phe  Gly  Phe  Val  Lys  Asp  Gly  Met  Asp  Thr  Val  Lys
3185                3190                3195                               3200

Lys  Ile  Glu  Ser  Phe  Gly  Ser  Pro  Lys  Gly  Ser  Val  Cys  Arg  Arg  Ile
               3205                3210                     3215

Thr  Ile  Thr  Glu  Cys  Gly  Gln  Ile
               3220
```

( 2 ) INFORMATION FOR SEQ ID NO:35:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:35:

```
Glu  Phe  Glu  Ser  Arg
 1                    5
```

( 2 ) INFORMATION FOR SEQ ID NO:36:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:36:

Thr Tyr Ser Ala Lys
1               5

(2) INFORMATION FOR SEQ ID NO:37:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:37:

Leu Asp Asn Ala Arg
1               5

(2) INFORMATION FOR SEQ ID NO:38:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:38:

Thr Tyr Ser Ala Lys
1               5

(2) INFORMATION FOR SEQ ID NO:39:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:39:

Asn Ile Tyr Ser Glu Glu Leu Arg
1               5

(2) INFORMATION FOR SEQ ID NO:40:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:40:

Thr Ala Leu Ser Glu Lys Arg
1               5

(2) INFORMATION FOR SEQ ID NO:41:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:41:

Leu Ala Leu Asp Met Glu Ile His Ala Tyr Arg
1               5                   10

( 2 ) INFORMATION FOR SEQ ID NO:42:

( i ) SEQUENCE CHARACTERISTICS:
  ( A ) LENGTH: 8 amino acids
  ( B ) TYPE: amino acid
  ( C ) STRANDEDNESS:
  ( D ) TOPOLOGY: linear ( i i ) MOLECULE TYPE: peptide ( x i ) SEQUENCE DESCRIPTION: SEQ ID NO:42:

Glu Met Ala Glu Met Arg Ala Arg
1               5

( 2 ) INFORMATION FOR SEQ ID NO:43:

( i ) SEQUENCE CHARACTERISTICS:
  ( A ) LENGTH: 15 amino acids
  ( B ) TYPE: amino acid
  ( C ) STRANDEDNESS:
  ( D ) TOPOLOGY: linear ( i i ) MOLECULE TYPE: peptide ( x i ) SEQUENCE DESCRIPTION: SEQ ID NO:43:

Glu Glu Leu Asp Phe Gln Lys Asn Ile Tyr Ser Glu Glu Leu Arg
1               5                   10                  15

( 2 ) INFORMATION FOR SEQ ID NO:44:

( i ) SEQUENCE CHARACTERISTICS:
  ( A ) LENGTH: 15 amino acids
  ( B ) TYPE: amino acid
  ( C ) STRANDEDNESS:
  ( D ) TOPOLOGY: linear ( i i ) MOLECULE TYPE: peptide ( x i ) SEQUENCE DESCRIPTION: SEQ ID NO:44:

Met Gln Gln Gln Leu Asp Glu Tyr Gln Glu Leu Leu Asp Ile Lys
1               5                   10                  15

( 2 ) INFORMATION FOR SEQ ID NO:45:

( i ) SEQUENCE CHARACTERISTICS:
  ( A ) LENGTH: 15 amino acids
  ( B ) TYPE: amino acid
  ( C ) STRANDEDNESS:
  ( D ) TOPOLOGY: linear ( i i ) MOLECULE TYPE: peptide ( x i ) SEQUENCE DESCRIPTION: SEQ ID NO:45:

Glu Glu Leu Asp Phe Gln Lys Asn Ile Tyr Ser Glu Glu Leu Arg
1               5                   10                  15

( 2 ) INFORMATION FOR SEQ ID NO:46:

( i ) SEQUENCE CHARACTERISTICS:
  ( A ) LENGTH: 515 amino acids
  ( B ) TYPE: amino acid
  ( C ) STRANDEDNESS:
  ( D ) TOPOLOGY: linear ( i i ) MOLECULE TYPE: peptide ( x i ) SEQUENCE DESCRIPTION: SEQ ID NO:46:

```
Thr Ala Leu Ser Glu Lys Arg Thr Leu Glu Gly Glu Leu His Asp Leu
 1               5                   10                  15
Arg Gly Gln Val Ala Lys Leu Glu Ala Ala Leu Gly Glu Ala Lys Lys
             20              25              30
Gln Leu Gln Asp Glu Met Leu Arg Arg Val Asp Ala Glu Asn Arg Leu
             35              40              45
Gln Thr Met Lys Glu Glu Leu Asp Phe Gln Lys Asn Ile Tyr Ser Glu
     50              55              60
Glu Leu Arg Glu Thr Lys Arg Arg His Glu Thr Arg Leu Val Glu Ile
65              70              75                          80
Asp Asn Gly Lys Gln Arg Glu Phe Glu Ser Arg Leu Ala Asp Ala Leu
             85              90                          95
Gln Glu Leu Arg Ala Gln His Glu Asp Gln Val Glu Gln Tyr Lys Lys
            100             105             110
Glu Leu Glu Lys Thr Tyr Ser Ala Lys Leu Asp Asn Ala Arg Gln Ser
            115             120             125
Ala Glu Arg Asn Ser Asn Leu Val Gly Ala Ala His Glu Glu Leu Gln
    130             135             140
Gln Ser Arg Ile Arg Ile Asp Ser Leu Ser Ala Gln Leu Ser Gln Leu
145             150             155                         160
Gln Lys Gln Leu Ala Ala Lys Glu Ala Lys Leu Arg Asp Leu Glu Asp
                165             170             175
Ser Leu Ala Arg Glu Arg Asp Thr Ser Arg Arg Leu Leu Ala Glu Lys
            180             185             190
Glu Arg Glu Met Ala Glu Met Arg Ala Arg Met Gln Gln Gln Leu Asp
            195             200             205
Glu Tyr Gln Glu Leu Leu Asp Ile Lys Leu Ala Leu Asp Met Glu Ile
    210             215             220
His Ala Tyr Arg Lys Leu Leu Glu Gly Glu Glu Arg Leu Arg Leu
225             230             235                         240
Ser Pro Ser Pro Thr Ser Gln Arg Ser Arg Gly Arg Ala Ser Ser His
            245             250             255
Ser Ser Gln Thr Gln Gly Gly Gly Ser Val Thr Lys Lys Arg Lys Leu
            260             265             270
Glu Ser Thr Glu Ser Arg Ser Ser Phe Ser Gln His Ala Arg Thr Ser
            275             280             285
Gly Arg Val Ala Val Glu Glu Val Asp Glu Glu Gly Lys Phe Val Arg
    290             295             300
Leu Arg Asn Lys Ser Asn Glu Asp Gln Ser Met Gly Asn Trp Gln Ile
305             310             315                         320
Lys Arg Gln Asn Gly Asp Asp Pro Leu Leu Thr Tyr Arg Phe Pro Pro
            325             330             335
Lys Phe Thr Leu Lys Ala Gly Gln Val Val Thr Ile Trp Ala Ala Gly
            340             345             350
Ala Gly Ala Thr His Ser Pro Pro Thr Asp Leu Val Trp Lys Ala Gln
            355             360             365
Asn Thr Trp Gly Cys Gly Asn Ser Leu Arg Thr Ala Leu Ile Asn Ser
    370             375             380
Thr Gly Glu Glu Val Ala Met Arg Lys Leu Val Arg Ser Val Thr Val
385             390             395                         400
Val Glu Asp Asp Glu Asp Glu Asp Gly Asp Asp Leu Leu His His His
            405             410             415
His Gly Ser His Cys Ser Ser Ser Gly Asp Pro Ala Glu Tyr Asn Leu
            420             425             430
```

| | | | | | | | | | | | | | | |
|---|---|---|---|---|---|---|---|---|---|---|---|---|---|---|
| Arg | Ser | Arg<br>435 | Thr | Val | Leu | Cys | Gly<br>440 | Thr | Cys | Gly | Gln | Pro<br>445 | Ala | Asp | Lys |
| Ala | Ser<br>450 | Ala | Ser | Gly | Ser | Gly<br>455 | Ala | Gln | Val | Gly | Gly<br>460 | Pro | Ile | Ser | Ser |
| Gly<br>465 | Ser | Ser | Ala | Ser | Ser<br>470 | Val | Thr | Val | Thr | Arg<br>475 | Ser | Tyr | Arg | Ser | Val<br>480 |
| Gly | Gly | Ser | Gly | Gly<br>485 | Gly | Ser | Phe | Gly | Asp<br>490 | Asn | Leu | Val | Thr | Arg<br>495 | Ser |
| Tyr | Leu | Leu | Gly<br>500 | Asn | Ser | Ser | Pro | Arg<br>505 | Thr | Gln | Ser | Pro | Gln<br>510 | Asn | Cys |
| Ser | Ile | Met<br>515 | | | | | | | | | | | | | |

What is claimed is:

1. A method of detecting cervical cancer in a human, the method comprising:

detecting in a sample isolated from said human the presence of a protein comprising an amino acid sequence selected from the group of sequences consisting of SEQ ID NO:19; SEQ ID NO:20; SEQ ID NO:21; SEQ ID NO:22; SEQ ID NO:23; SEQ ID NO:24; SEQ ID NO:25; and SEQ ID NO:26, the presence of said protein being indicative of cervical cancer in said human.

2. The method of claim 1, wherein said protein comprises the amino acid sequence set forth in SEQ ID NO:19.

3. The method of claim 1, wherein said protein comprises the amino acid sequence set forth in SEQ ID NO:20.

4. The method of claim 1, wherein said protein comprises the amino acid sequence set forth in SEQ ID NO:21.

5. The method of claim 1, wherein said protein comprises the amino acid sequence set forth in SEQ ID NO:22.

6. The method of claim 1, wherein said protein comprises the amino acid sequence set forth in SEQ ID NO:23.

7. The method of claim 1, wherein said protein comprises the amino acid sequence set forth in SEQ ID NO:24.

8. The method of claim 1, wherein said protein comprises the amino acid sequence set forth in SEQ ID NO:25.

9. The method of claim 1, wherein said protein comprises the amino acid sequence set forth in SEQ ID NO:26.

10. The method of claim 1, wherein said sample is a tissue or body fluid sample.

11. The method of claim 1, wherein said sample is a biopsy sample.

12. The method of claim 1, wherein said sample is a cervical cell sample.

13. The method of claim 1, wherein said sample is a Papanicolaou smear.

14. A method of detecting cervical cancer in a human, the method comprising the steps of:

(a) contacting a sample derived from said human with a binding moiety that binds specifically to a cervical cancer-associated protein to produce a binding moiety-cervical cancer-associated protein complex, wherein said binding moiety is selected from the group consisting of an antibody, an antibody fragment and a biosynthetic antibody binding site, and wherein said binding moiety binds specifically to a protein comprising the amino acid sequence set forth in SEQ ID NO:26; and (b) detecting the presence of said complex, the presence of said complex being indicative of the presence of cervical cancer in said human.

15. The method of claim 14, wherein said cervical cancer-associated protein is further characterized as being detectable at a higher level in a human cervical cancer cell than in a normal human cervical cell, as determined by two dimensional gel electrophoresis.

16. The method of claim 14, wherein said sample is a tissue or body fluid sample.

17. The method of claim 14, wherein said sample is a biopsy sample.

18. The method of claim 14, wherein said sample is a Papanicolaou smear.

19. The method of claim 14, wherein said sample is a cervical cell sample.

20. The method of claim 14, wherein said binding moiety is an antibody.

21. The method of claim 20, wherein said antibody is a monoclonal antibody.

22. The method of claim 20, wherein said antibody is labeled with a detectable moiety.

23. The method of claim 21, wherein said monoclonal antibody is labeled with a detectable moiety.

* * * * *